(12) United States Patent
Sooknanan

(10) Patent No.: US 8,304,183 B2
(45) Date of Patent: Nov. 6, 2012

(54) SELECTIVE TERMINAL TAGGING OF NUCLEIC ACIDS

(75) Inventor: Roy R. Sooknanan, Beaconsfield (CA)

(73) Assignee: Cellscript, Inc., Madison, WI (US)

( * ) Notice: Subject to any disclaimer, the term of this patent is extended or adjusted under 35 U.S.C. 154(b) by 697 days.

(21) Appl. No.: 12/095,409

(22) PCT Filed: Nov. 30, 2005

(86) PCT No.: PCT/CA2005/001830
§ 371 (c)(1),
(2), (4) Date: Sep. 22, 2008

(87) PCT Pub. No.: WO2007/062495
PCT Pub. Date: Jun. 7, 2007

(65) Prior Publication Data
US 2009/0227009 A1    Sep. 10, 2009

(51) Int. Cl.
*C12Q 1/68*     (2006.01)
*C12P 19/34*   (2006.01)
*C12N 15/64*   (2006.01)
*C07H 21/02*   (2006.01)
*C07H 21/04*   (2006.01)

(52) U.S. Cl. .... 435/6.1; 435/91.1; 435/91.4; 435/91.42; 536/23.1; 536/24.2

(58) Field of Classification Search .......... None
See application file for complete search history.

(56) References Cited

U.S. PATENT DOCUMENTS

| | | | |
|---|---|---|---|
| 5,545,522 A | 8/1996 | Van Gelder et al. | |
| 5,597,713 A | 1/1997 | Kato et al. | |
| 5,962,272 A | 10/1999 | Chenchik et al. | |
| 6,132,997 A | 10/2000 | Shannon | |
| 6,383,777 B1 * | 5/2002 | Breyer et al. | 435/69.1 |
| 2005/0153333 A1 | 7/2005 | Sooknanan | |

FOREIGN PATENT DOCUMENTS

| | | |
|---|---|---|
| WO | 9222663 | 12/1992 |
| WO | 0006779 | 2/2000 |
| WO | 03012142 | 2/2003 |
| WO | 2005098044 | 10/2005 |

OTHER PUBLICATIONS

Vasquez, et al. (2001) Arch Virol, 146: 59-69.*
Ren, et al. (2001) Journal of the American Chemical Society, 123: 6742-43.*
Botero, et al. (2005) Applied and Environmental Microbiology, 71(3): 1267-75.*
Gubler et al., Gene, (1983), 25:263-269.
Dumas Milne Edwards et al., Nucleic Acids Res. (1991) 19, 5227-5232.

* cited by examiner

*Primary Examiner* — Robert M Kelly

(57) ABSTRACT

Methods are provided for adding a terminal sequence tag to nucleic acid molecules for use in RNA or DNA amplification. The tag introduced may be used as a primer binding site for subsequent amplification of the DNA molecule and/or sequencing of the DNA molecule and therefore provides means for identification and cloning of the 5'-end or the complete sequence of mRNAs.

12 Claims, 13 Drawing Sheets

1650 bp →
300 bp →

1761 nt →

β-actin 1272 nt →

Gapdh

Gapdh

β-actin

Cathepsin K full-length RNA

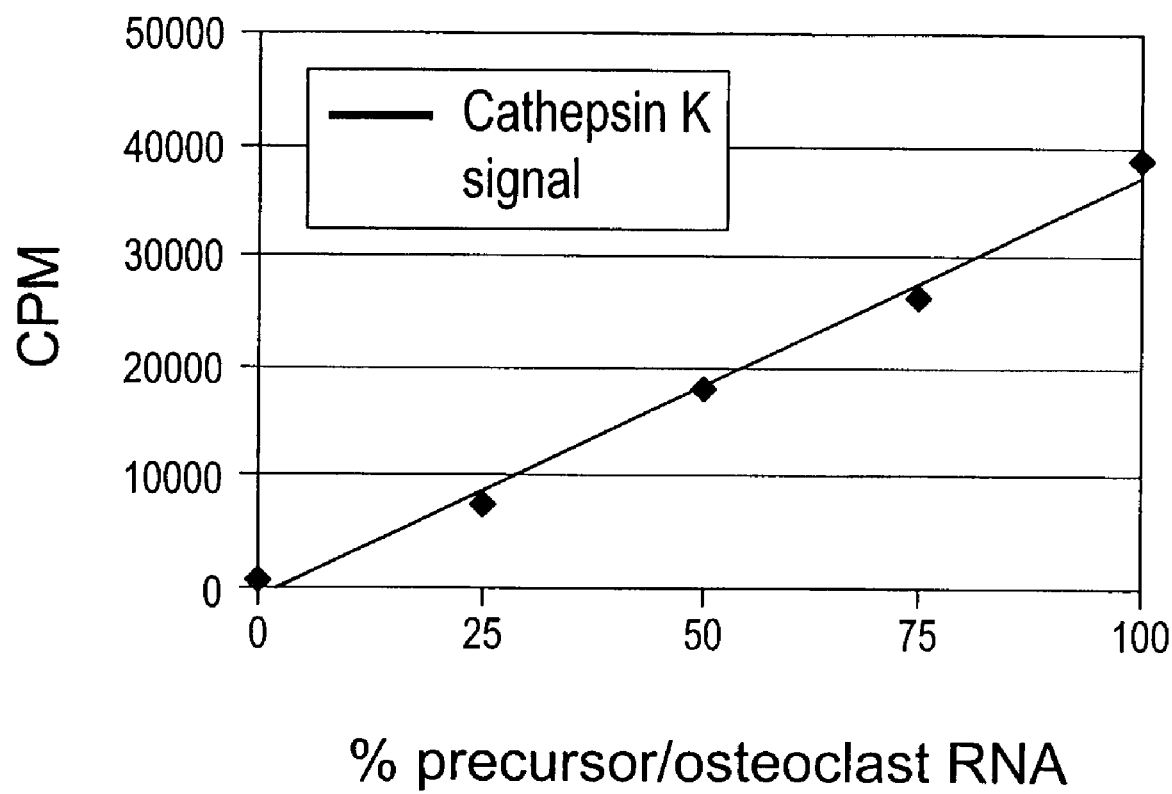
FIG_8

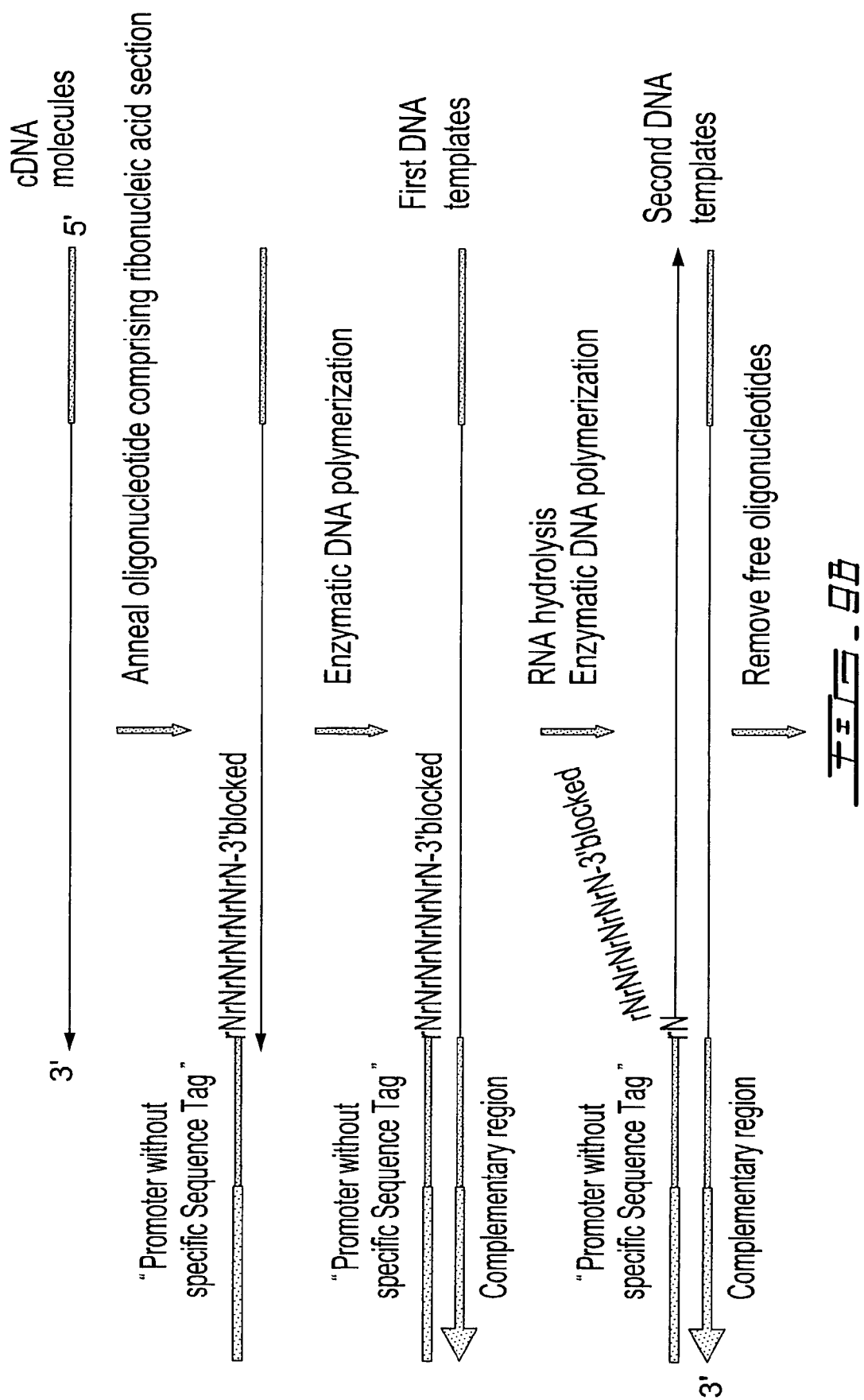

Agarose gel
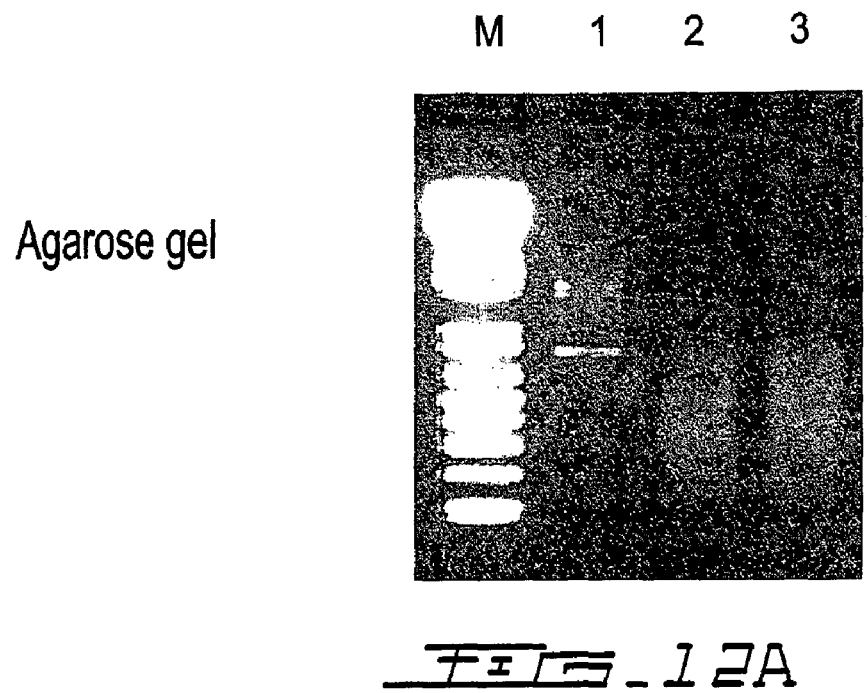
FIG. 12A
Northern blots
GAPDH probe  ← Full-length
TRAP probe  ← Full-length
FIG. 12B

SELECTIVE TERMINAL TAGGING OF NUCLEIC ACIDS

FIELD OF THE INVENTION

This invention relates to a method for adding a terminal sequence tag to nucleic acid molecules and uses thereof for RNA transcription or DNA amplification, cloning or sequencing and identification of target nucleic acid molecules.

BACKGROUND OF THE INVENTION

One of the more persistent objectives in molecular biology has been determining the nucleic acid sequence and relative abundance of individual species in heterogeneous mRNA populations. Methods for determining mRNA sequences typically involve analyzing the DNA sequence of single clones of a cDNA library, which are derived by enzymatic production of double-stranded cDNA from the mRNA. Methods for determining the relative abundance of mRNA species typically involve quantifying the hybridization of a defined nucleic acid sequence to a complementary sequence in the mRNA population. Analysis of samples containing a relatively low quantity of mRNA generally involves amplification prior to the application of methods for determining the sequence or relative abundance, of particular mRNA species. Amplification methods that proceed with linear kinetics during the course of the amplification reaction are less likely to introduce bias in the relative levels of different mRNAs than those that proceed with exponential kinetics (Shannon, U.S. Pat. No. 6,132,997).

In Van Gelder et al., U.S. Pat. No. 5,545,522, a process is described for amplifying a target nucleic acid sequence using a single primer-promoter, an oligonucleotide that has a sequence complementary to an RNA polymerase promoter linked to a sequence complementary to the target nucleic acid sequence. In an embodiment of this process, poly(A)+ mRNA is the target nucleic acid, with a primer-promoter having a 3'-terminal oligo(dT) sequence, for the amplification of "antisense RNA", RNA transcripts that are complementary to the original mRNA. In this embodiment, cDNA is synthesized from the mRNA by extension of the annealed primer-promoter using reverse transcriptase; the RNA strand of the resulting mRNA:cDNA hybrid is partially hydrolyzed using RNase H; a second strand of DNA is synthesized from the cDNA by extension of the annealed mRNA fragments using DNA polymerase I (Gubler et al. (1983) Gene 25:263-269); and multiple copies of antisense RNA are synthesized from the second strand of DNA using an RNA polymerase. One problem with this method is that the 5' ends of the mRNA, which become used as primers for second strand DNA synthesis, cannot be amplified and therefore cannot be identified. For 5'-terminal mRNA sequences to be included in an amplified product, an arbitrary sequence, a "sequence tag", needs to be added to either the 5' ends of the mRNA or the 3' ends of the cDNA. This sequence tag provides a terminal priming site needed for amplification of the cDNA that was synthesized from the initial priming site, typically the 3'-terminal poly(A) of mRNA. Three general methods for providing a terminal priming site on mRNA or cDNA for the purposes of nucleic acid amplification are described below. Other methods based upon adding terminal polymer or oligomer tracts composed of the same nucleotide using enzymes such as terminal transfer or polyadenylate polymerase, "tailing methods", are more applicable for cloning rather than amplifying nucleic acid molecules, and are thus not included.

In Kato et al., U.S. Pat. No. 5,597,713, a process is described for adding an arbitrary sequence to the 5' ends of mRNA. In this process, mRNA is pretreated using a phosphatase to remove any terminal phosphates, the 5-'terminal cap is removed from the mRNA using a pyrophosphatase, and an oligonucleotide, having an arbitrary sequence composed of DNA and/or RNA, is added to the resulting 5'-terminal phosphate of the mRNA using T4 RNA ligase. In an embodiment of this process, cDNA having a 3'-terminal arbitrary sequence is synthesized from the ligated mRNA products by extension of an annealed oligo(dT) primer using reverse transcriptase. Since this process requires the performance of two hydrolytic steps on the mRNA, any contaminating hydrolytic activities in the enzymes and the alkaline reaction conditions can cause the loss of intact mRNA. In addition, T4 RNA ligase is less efficient with longer nucleic acid substrates.

In Dumas Milne Edwards et al. 1991 (Nucleic Acids Res. 19, 5227-5232) a process is described for amplifying 5'-terminal sequences of mRNA whereby an arbitrary sequence is added to the 3' ends of cDNA. In this process, cDNA is synthesized from mRNA by extension of an annealed primer having a 3'-terminal oligo(dT) linked to a 41-nt arbitrary sequence using reverse transcriptase. After removing the mRNA from the resulting hybrid, an oligodeoxyribonucleotide, having a 44-nt arbitrary sequence, a 5'-terminal phosphate and a blocked 3' end, is added to the 3' ends of the cDNA using T4 RNA ligase. The ligated cDNA products, each with a different arbitrary sequence at each end, are amplified using PCR with primers derived from the 5'-terminal half of each arbitrary sequence. The resulting amplified products are purified and amplified using a second PCR this time with nested primers derived from the 3'-terminal half of each arbitrary sequence. For this process to work the optimum reaction conditions needed to be modified so that cDNA can be used as acceptor by T4 RNA ligase, resulting in the inefficient production of ligated cDNA as evidenced by the extensive exponential amplification that is required for their detection.

In Chenchik et al., U.S. Pat. No. 5,962,272, a process is described for the synthesis and cloning of cDNA corresponding to the 5' ends of mRNA using a template-switching oligonucleotide that hybridizes to the 5'-terminal CAP of mRNA. The method comprises contacting RNA with a cDNA synthesis primer which can anneal to RNA, a suitable enzyme which possesses reverse transcriptase activity, and a template switching oligonucleotide under conditions sufficient to permit the template-dependent extension of the primer to generate an mRNA:cDNA hybrid. The template switching oligonucleotide hybridizes to the CAP site at the 5' end of the RNA molecule and serves as a short, extended template for CAP-dependent extension of the 3'-end of the single stranded cDNA that is complementary to the template switching oligonucleotide. The resulting full-length single stranded cDNA includes the complete 5'-end of the RNA molecule as well as the sequence complementary to the template switching oligonucleotide, which can then serve as a universal priming site in subsequent amplification of the cDNA. The template switching oligonucleotide hybridizes to the CAP site at the 5' end of the mRNA and forms basepair(s) with at least one nucleotide at the 3' end of the cDNA of an mRNA-cDNA intermediate. Since this process is based upon the specific interaction with the CAP of an mRNA and the 3' end of a cDNA in an mRNA-cDNA intermediate, it is unlikely to be applicable for adding terminal sequence tags to nucleic acid molecules that are single-stranded or are without a CAP structure.

The above is a cursory sampling of the methods that have been developed for the amplification of nucleic acid molecules. The person of skill in the art will be familiar with many of them and will also be familiar with their shortcomings. Some examples of the shortcomings include the sequence bias of exponential amplification and the inefficiency of single-stranded ligation; the narrow applicability to a few forms of RNA and DNA; and the requirement of a 5'-terminal CAP or an mRNA-cDNA intermediate. Notwithstanding the wide use of these amplification processes, a need exists for improvements. The research that is ongoing in this art is indicative of the search for a substantially universal method that can be broadly applied to unknown sequences in samples containing whole extractions of nucleic acids. Thus there is a need for a process that is capable of sensitive amplification of sequences from the entire mRNA, particularly from the 5' ends.

The present invention seeks to meet these needs and other needs.

SUMMARY OF THE INVENTION

It is an object of the present invention to provide novel methods, kits and reagents for adding a terminal sequence tag to nucleic acid molecules and uses thereof in RNA transcription or DNA amplification, which obviates or mitigates at least one of the disadvantages of the prior art.

The present invention provides methods, kits and reagents for adding at least one terminal nucleic acid sequence (a sequence tag) to target nucleic acid molecules.

Exemplary Embodiments of First Oligonucleotides

The present invention, provides in a first aspect thereof, a first oligonucleotide which may comprise sequentially (in a 5'->3' direction), an overhanging portion and an hybridizing portion.

The present invention, more particularly relates to a first oligonucleotide which may comprise;
  i) an overhanging portion which may comprise, for example, a first sequence tag and;
  ii) an hybridizing portion which may be able to hybridize to at least one target nucleic acid molecule.

In accordance with the present invention, the overhanging portion may be substantially non-hybridizable to a target nucleic acid molecule. Alternatively, the overhanging portion may be substantially non-hybridized to a target nucleic acid molecule upon hybridization of the hybridizing portion with the target nucleic acid molecule.

In accordance with the present invention, the overhanging portion may comprise, for example, one or more sequence tags. The overhanging portion may be able to serve as a template for a polymerase, such as for example, a DNA polymerase.

Further in accordance with the present invention, the first sequence tag may comprise a sequence which is defined in accordance with the need of the user (a user-defined sequence), and although exemplary first sequence tags are given herein, it is to be understood that the choice of the first sequence tag is not intended to be limited.

Also in accordance with the present invention, the hybridizing portion may comprise, for example, a nucleic acid sequence selected from the group consisting of 1) a random sequence and 2) a nucleic acid sequence substantially complementary (e.g., 80 to 100% complementarity over the entire sequence or portion of sequences) to a portion located at a 3'-end of a target nucleic acid molecule (with respect to the 5'->3' direction).

The sequence tag may be located near the 5'-end of the first oligonucleotide and the hybridizing portion may be located near the 3'-end of the first oligonucleotide.

The hybridizing portion may be able, more particularly to hybridize to the 3'-end of a target nucleic acid molecule in such a manner that the overhanging portion extends past the 3'-end of the target.

In accordance with the present invention, the first oligonucleotide may also comprise a blocked 3'-end (3'-terminus). The blocked 3'-end may prevent, for example, the first oligonucleotide from functioning as a primer for primer extension using the first templates as template.

The present invention also relates to a plurality of first oligonucleotides each of which may comprise;
  i) an overhanging portion which may comprise a first sequence tag and;
  ii) an hybridizing portion which may be able to hybridize to at least one target nucleic acid molecule.

In accordance with the present invention, the plurality of first oligonucleotides may each comprise a blocked 3'-end.

Further in accordance with the present invention, the hybridizing portion of each of first oligonucleotides may comprise, for example, a random sequence. The random sequence of each of the first oligonucleotides may be, for example, substantially different from one another (in terms of nucleic acid composition and/or length, etc.).

Alternatively, the hybridizing portion of each of first oligonucleotides may comprise, for example, a nucleic acid sequence substantially complementary (e.g., 80 to 100% complementarity over the entire sequence or portion of sequences) to a portion located at a 3'-end of a target nucleic acid molecule.

The first sequence tag of each of the first oligonucleotides may be identical or substantially identical (e.g., 80 to 100% sequence identity) to one another or to a portion thereof. In some circumstances, it may be useful that the first sequence tag comprises a sequence complementary to a desired sequence.

In accordance with the present invention, the first sequence tag may comprise, for example, a promoter sequence.

Also, in accordance with the present invention, the first sequence tag may be a promoter sequence.

The promoter sequence may be selected, for example, from the group consisting of a RNA polymerase promoter sequence, a DNA polymerase promoter sequence etc.

Further in accordance with the present invention, the RNA polymerase promoter sequence may be selected, for example and without limitation, from the group consisting of bacteriophage RNA polymerases promoters such as, the bacteriophage T7 RNA polymerase, the phage T3 RNA polymerase, the *Salmonella* phage sp6 RNA polymerase etc.

The first oligonucleotide may comprise, for example, a promoter and initiation sequences which may be specific for a desired RNA polymerase.

It will occur to those of skill in the art that other suitable promoter and initiation sequences may be used to achieve desirable levels of transcription of RNA as described herein.

When the nucleic acid target is a mRNA, the hybridizing portion is preferably not a oligo(dT) sequence or if a oligo(dT) is used, the 3'-end may preferably be blocked.

As discussed herein the first sequence tag is not intended to be limitative and may be an arbitrary sequence having any combination of purines and pyrimidines, including but not limited to G, A, T or C (natural or modified) arranged to form a sequence of any desired length. The sequence tag may be defined by the user to have a specific length and base composition to provide a template for accurate extension of the nucleic acid molecules.

The sequence tag may be deoxy- and/or ribonucleotides as long as it provides a template for the enzymatic extension of the nucleic acid molecules.

The sequence tag may, for example, be substantially free of symmetry elements, such as direct and inverse repeats, and it may provide a template for extension of the nucleic molecules in forming a 3'-terminal sequence tag. Once the complementary sequence of the first sequence tag is introduced in a target nucleic acid molecule, it may provide a suitable sequence that may be used as a site for hybridizing and extending an oligonucleotide primer or for hybridizing an oligonucleotide template, which may be used for extension or detection of the tagged nucleic acid molecules or for other purposes. It is therefore to be understood herein that the sequence tag portion of the oligonucleotide may comprise a sequence defined by the user to carry out the different steps of a method of the present invention, however any suitable sequence tag may be used to carry out the method of the present invention and this portion of the oligonucleotide is not intended to be limited to a specific nucleotide sequence.

As may be understood from the above, the sequence tag may provide the nucleic acid molecule with a defined sequence at its terminus and this sequence tag may subsequently serve as an hybridization site (a means for hybridizing) for 1) subsequent amplification of the nucleic acid molecule with a primer that comprises a nucleic acid sequence complementary to the sequence tag, 2) subsequent add a further desired sequence to the nucleic acid molecule by using the methods described herein, etc.

Alternatively, the first sequence tag may comprise a functional sequence such as a RNA polymerase promoter sequence and therefore may directly be used to amplify RNA from the tagged nucleic acid target.

The random sequence portion of the first oligonucleotide may be any number of nucleotides in length such as between about 4 and about 9 (or from about 4 to 15). The random sequence may comprise an equal representation of G, A, T and C at each of the different positions. Wobble bases such as inosine (I) may also be used instead of the standard bases at any of the positions.

In addition, one or more of the nucleotides contained in the random sequence may be chemically modified for example, 2'-O methylated nucleotides, phosphorothioates or any such chemical modifications that render the nucleotide(s) inert to nucleases.

As discussed herein, the first oligonucleotide may comprise a blocked 3'-end. Thus, the 3' terminus of the oligonucleotides may be chemically blocked with, for example, C3 propyl spacer, amine group ($NH_2$), phosphate or any other chemical modifications that render the oligonucleotide mixture inert as a primer for primer extension using either a DNA- or RNA-directed DNA polymerase.

The present invention also provides a plurality of first oligonucleotides each first oligonucleotides may comprise 1) one or more first sequence tag and 2) hybridizing portion selected from the group consisting of a random sequence and a nucleic acid sequence substantially complementary to a portion (of a target) located at a 3'-end of the target nucleic acid molecule (with respect to the 5'->3' direction) and combination thereof.

In accordance with the present invention, the hybridizing portion of each of the first oligonucleotides may be the same or different. For example, several different sequence tags (a plurality of user defined sequence tags) may be added simultaneously to a known target nucleic acid molecule and therefore the oligonucleotide used in the present method may comprise a specific hybridizing portion able which is substantially complementary to a portion (of a target) located at a 3'-end of the target nucleic acid molecule and a plurality of user defined sequence tags.

Each of the nucleic acid sequence substantially complementary to a portion of a target nucleic acid molecule located at a 3-'end of the target may be the same or different from one another.

It is particularly to be understood herein that when the nucleic acid sequence of the target nucleic acid molecule is known, the first oligonucleotide may be composed of nucleic acid sequence defined by the user (e.g., a specific nucleic acid sequence may be used to carry the methods of the present invention). In a particular embodiment of the present invention, the hybridizing portion may be defined to be complementary to a corresponding portion of a known nucleic acid target sequence. Therefore, a portion of the known sequence of a target nucleic acid which is located at the 3'-end (e.g., extreme 3'-end (or terminal sequence)) of the target may be used to design a complementary hybridizing portion.

However, even if the sequence of the target nucleic acid is known, a suitable hybridizing portion of the first oligonucleotides may also be composed of a random sequence. In order to increase the chance of tagging a known target nucleic acid with an oligonucleotide comprising a random sequence, a mixture of first oligonucleotides comprising a library of random sequences attached to the first sequence tag may be used.

Alternatively, it is to be understood herein that when the nucleic acid sequence of the target nucleic acid molecule is unknown, the sequence of the first oligonucleotide used for terminal tagging may preferably comprise random sequences.

The target nucleic acids may encompass unique species or multiple species. The first oligonucleotides used to add a terminal tag to unique or multiple species the same to those described above. It is to be understood herein that when a terminal tag is to be added to multiple species contained within a sample (solution, tissue, etc.) a plurality of first oligonucleotides comprising: 1) a first sequence tag and 2) a random sequence, may be used. Again in order to increase the chance to add a tag to several unrelated species (multiple species) of target nucleic acid molecules, the random sequence of each of the first oligonucleotides may preferably be different.

The present invention thus provides in a further aspect, a plurality of first oligonucleotides each first oligonucleotides may comprise; 1) an identical sequence tag and 2) a different random sequence. In accordance with the present invention, the first oligonucleotides may further comprise a blocked 3'-end.

Exemplary Embodiments of Second Oligonucleotides

The present invention also relates to the addition of a second sequence tag to a first template. The second sequence tag may be added, for example, to a first template comprising a first sequence tag.

The present invention relates in a further aspect thereof, to a second oligonucleotide which may comprise;
i) an overhanging portion which may comprise a second sequence tag (a desired sequence or a sequence of interest); and
ii) an hybridizing portion which may comprise a first sequence tag.

In accordance with the present invention, the overhanging portion may be substantially non-hybridizable to a target nucleic acid molecule or first template. Alternatively, the overhanging portion may be substantially non-hybridized to a target nucleic acid molecule or first template upon hybridization of the hybridizing portion with the target nucleic acid molecule or first template.

Further in accordance with the present invention, the overhanging portion (second sequence tag) may serve as a template for a polymerase.

The second oligonucleotide may comprise sequentially (in a 5'->3' direction); a) a 5'-overhanging portion which may comprise a second sequence tag (a desired sequence or sequence of interest) and; b) an hybridizing portion which may comprise a first sequence tag.

In accordance with the present invention, the second oligonucleotide may further comprise a blocked 3' (a blocked 3'-terminus). The blocked 3' terminus may prevent, for example, the second oligonucleotide from functioning as a primer for primer extension using the first templates as template.

In accordance with the present invention, the hybridizing portion may be at the 3'-end of the oligonucleotide. Further in accordance with the present invention, the overhanging portion may be located at the 5'-end of the second oligonucleotide and the hybridizing portion may be located at the 3'-end of the second oligonucleotide. For example, the overhanging portion may be 5' relative to the hybridizing portion.

It is to be understood herein that the first sequence tag of the second oligonucleotide may be identical or substantially identical to the first sequence tag of the first oligonucleotide or to portions thereof. It is therefore, to be understood herein that the first sequence tag may be substantially complementary to the complementary first sequence tag or portions thereof of the first template.

In accordance with the present invention, the second sequence tag (desired sequence or sequence of interest) may be, for example, selected from the group consisting of a promoter sequence, a restriction site, or any other sequence of choice and combination of several sequences of choice.

The second sequence tag may comprise, more particularly, a promoter sequence.

In accordance with the present invention, the promoter sequence may comprise for example, a RNA polymerase promoter sequence, a DNA polymerase promoter sequence etc.

Further in accordance with the present invention, the RNA polymerase promoter sequence may be selected, for example and without limitation, from the group consisting of bacteriophage RNA polymerases promoters such as, a T7 RNA polymerase promoter sequence, a sp6 RNA polymerase promoter sequence, etc.

In accordance with an embodiment of the invention, the second oligonucleotide may comprise a promoter and initiation sequences which may be specific for a desired RNA polymerase such as the bacteriophage T7 RNA polymerase, the phage T3 RNA polymerase, the *Salmonella* phage sp6 RNA polymerase, etc.

It will occur to those of skill in the art that other suitable promoter and initiation sequences may be used to achieve desirable levels of transcription of RNA as described herein.

The second sequence tag may be of a particular length and base composition to allow specific and efficient annealing to the (complementary first) sequence tag of the first template under conditions, including those of an enzymatic DNA polymerization reaction.

The second oligonucleotide may thus comprise, for example, in its overhanging portion, a sequence of interest such as the plus (+) sense sequence of a promoter and its transcription initiation site. The promoter template may be of a particular length and base composition to allow specific and desirable synthesis of double-stranded promoters by extension of the first template under the conditions of an enzymatic DNA polymerization reaction. The resulting double-stranded promoter may contain sufficient information to allow specific and desirable (operative) binding of a RNA polymerase and initiation of transcription at the desired site.

Further in accordance with the present invention, the second sequence tag may be a sequence allowing for its (operative) recognition and cleavage by a restriction endonuclease site. The restriction endonuclease site may be located, for example, at a 5-terminus (5'-end) or may be embedded within the second oligonucleotides.

In some circumstances, it may be useful that the first sequence tag comprises a sequence complementary to a desired sequence.

It is to be understood herein that the overhanging portion (5'-overhanging portion) and the hybridizing portion of oligonucleotides of the present invention may be covalently attached to each other. More particularly, the overhanging portion (5'-overhanging portion) and the hybridizing portion may be made of consecutive nucleic acid separated or not by other nucleic acids or other type of spacers.

In accordance with the present invention, the oligonucleotides of the present invention may also have a 3'-terminal sequence that reduces annealing to itself or another primer in the reaction such that a primer would be extended using itself or another primer as template in a DNA or RNA amplification reaction, hence producing what is described in the art as "primer-dimers".

Exemplary Embodiments of Target Nucleic Acid Molecules

The target nucleic molecules may be any type of nucleic acid having an end (3'-end) extendable by a polymerase. The target nucleic acid molecule may also have a portion substantially complementary to a first or second oligonucleotide.

The target nucleic acid may be composed of natural nucleic acids or modified nucleic acids.

In accordance with the present invention, the target nucleic acid molecule may be for example, a RNA molecule, a DNA molecule, a RNA/DNA hybrid, etc.

It is to be understood herein that several types of DNA molecule may be used to carry out the present invention, such as for example and without limitation, a single-stranded DNA molecule, a double-stranded DNA molecule, a partially double-(and single) stranded DNA molecule, a DNA/RNA hybrid, DNA library etc.

For the purpose of the present invention, when the DNA molecule is double-stranded, the method of the present invention may comprise a step of transforming the double-stranded DNA molecule into a substantially single-stranded DNA molecule. Double-stranded DNA may be made single-stranded by using, for example, chemical, enzymatic, mechanical or thermal methods. It is also to be understood herein that DNA molecules may originate from various sources, including without limitation, mammalian genomic DNA (human, animal, etc.), cDNA, bacterial DNA, viral DNA, insect DNA, etc.

A target RNA molecule may be any ribonucleic acid molecule or library of ribonucleic acid molecules containing a 3'-OH group. In accordance with the present invention, the RNA molecules may be for example and without limitation, a messenger RNA (mRNA), a heterogeneous nuclear RNA (hnRNA), ribosomal RNA (rRNA), transfer RNA (tRNA), bacterial RNA, viral RNA, single-stranded RNA, double-stranded RNA, antisense-RNA etc. Double-stranded RNA may be made single-stranded by using chemical, enzymatic, mechanical or thermal methods.

In a particular embodiment of the present invention, the RNA molecule is a mRNA. In an additionally particular embodiment of the present invention, the DNA molecule is a complementary DNA (cDNA).

An initial mRNA target may be transformed in a cDNA target by using standard methods of reverse transcription known in the art. For example, cDNA molecules may be formed by contacting a mixture containing mRNA with a primer comprising a terminal sequence substantially complementary to the mRNA, under conditions such that, the terminal sequence of the primer anneals with the mRNA and is extended using the mRNA as template.

This method is commonly effected and may be performed for example, by using a oligo(dT) primer which hybridizes to the poly-A tail found at the 3'-end of eukaryotic mRNA and an enzyme which may suitably use a mRNA as template to generate a complementary DNA molecule. A suitable enzyme having these characteristic is, for example, a Reverse transcriptase enzyme.

Alternatively, when the sequence of the target mRNA is known, a primer complementary to the 3'-end of the known target mRNA may be used to generate a cDNA.

The cDNA may be prepared from total RNA or purified mRNA containing a single or multiple species, using an oligo (dT) as primer and reverse transcriptase for extending the primer. The RNA may be removed from the cDNA by using chemical, enzymatic, mechanical or thermal methods.

It is also to be understood herein, that non polyA-containing RNA may be transformed into a cDNA by using an oligonucleotide which hybridizes to a known sequence substantially near a 3'-end.

Exemplary Embodiments of Methods

The present invention also relates to methods for adding a sequence tag to target nucleic acid molecules. For example, using the method of the present invention, a terminal tag may be added to the 3'-end of a target nucleic acid molecule.

The present invention provides in one aspect thereof, a method for adding a sequence tag (a terminal sequence tag) to a target nucleic acid molecule, the method may comprise, for example, contacting the target nucleic acid molecule with at least one oligonucleotide which may comprise;
  i) a 5'-overhanging portion comprising a sequence tag, and;
  ii) an hybridizing portion which may be selected from the group consisting of a) a random sequence, and; b) a sequence which may be substantially complementary to a portion (of a target nucleic acid molecule) located, for example, at a 3'-end of the target nucleic acid molecule,
under conditions which may allow hybridization (annealing) of the hybridizing portion with the target nucleic acid molecule.

More particularly, the present invention relates to a method for adding a sequence tag to a target nucleic acid molecule, the method may comprise; contacting the target nucleic acid molecule with at least one oligonucleotide which may comprise;
  i) a 5'-overhanging portion comprising a sequence tag, and;
  ii) an hybridizing portion comprising a random sequence, under conditions allowing hybridization (annealing) of the hybridizing portion with the target nucleic acid molecule.

Also more particularly, the present invention relates to a method for adding a sequence tag to a target nucleic acid molecule which may comprise; contacting the target nucleic acid molecule with at least one oligonucleotide which may comprise;
  i) a 5'-overhanging portion comprising the sequence tag, and;
  ii) an hybridizing portion comprising a sequence substantially complementary to a portion located at a 3'-end of the of a target nucleic acid molecule,
under conditions which may allow hybridization (annealing) of the hybridizing portion with the target nucleic acid molecule.

In accordance with the present invention, the method may further comprise a step of: extending the target nucleic acid molecule and at least one oligonucleotide. The method may, for example, further comprise a step of; extending the target nucleic acid molecule whereby the oligonucleotide may remain unextended.

In accordance with the present invention at least one oligonucleotide may further comprise a blocked 3'-end.

In accordance with the present invention, the method may further comprise a step of: extending the target nucleic acid molecule to generate a first template comprising a complementary first sequence tag whereby the oligonucleotide may remain unextended.

The present invention also particularly relates to a method wherein a plurality of target nucleic acid molecules may each be tagged, the method may comprise the step of contacting the plurality of target nucleic acid molecules with a plurality of oligonucleotides each comprising;
  i) a 5'-overhanging portion comprising a sequence tag, and;
  ii) an hybridizing portion selected from the group consisting of a) a random sequence and b) a sequence substantially complementary to a portion of a target nucleic acid molecule located at a 3'-end of the target,
under conditions which may allow hybridization of the hybridizing portion (a second portion) with the target nucleic acid molecules.

Also, more particularly, the present invention relates to a method wherein a plurality of target nucleic acid molecules may each be tagged, the method may comprise the step of contacting the plurality of target nucleic acid molecules with a plurality of oligonucleotides each comprising;
  i) a 5'-overhanging portion comprising a sequence tag, and;
  ii) an hybridizing portion comprising a random sequence, under conditions which may allow hybridization of the hybridizing portion with the target nucleic acid molecules.

In accordance with the present invention, the method may comprise a step of extending the plurality of target nucleic acid molecules.

The present invention provides in a further aspect thereof, a method for adding a terminal sequence tag to a target nucleic acid molecule which may comprise the steps of, for example;
  a. contacting the nucleic acid molecule with an oligonucleotide which may comprise (include), for example;
    i. a 5'-overhanging portion which may include a first sequence tag;
    ii. an hybridizing portion which may be able to hybridize to the target nucleic acid molecule, and;
    iii. a blocked 3'-end,
  the contacting step may be effected under conditions which may allow hybridization (annealing) of the hybridizing portion with the target nucleic acid molecule and;
  b. extending the target nucleic acid molecule to generate a first template comprising a complementary first sequence tag.

The present invention provides in an additional aspect thereof, a method for adding a terminal sequence tag to a plurality of target nucleic acid molecules, the method may comprise the steps of, for example a. contacting the plurality of nucleic acid molecules with a plurality of oligonucleotides each of which may comprise, for example;
   i. a 5'-overhanging portion which may comprise a first sequence tag;
   ii. an hybridizing portion which may be able to hybridize to a target nucleic acid molecule and;
   iii. a blocked 3'-end,
   wherein the contacting step may be effected under conditions which may allow hybridization of the hybridizing portion with the target nucleic acid molecule and;
b. extending the plurality of target nucleic acid molecules to generate a plurality of first templates each comprising a complementary first sequence tag.

The method may further comprise the step of carrying extension of the target nucleic acid molecule by providing the mixture of target and first oligonucleotide with conditions and reagents allowing extension.

In accordance with the present invention, the extension step may be performed by a polymerase as described herein.

Exemplary embodiments of oligonucleotides used in the present methods are as described herein. For example, a first oligonucleotides may be used in the exemplary embodiments of the method of the present invention.

In accordance with the present invention, the hybridizing portion of the oligonucleotide may be able to hybridize at the 3'-end of the target nucleic acid molecule, for example at the extreme 3'-end.

Further in accordance with the present invention, the 5'-overhanging portion of the oligonucleotide may serve as a template for a ribonucleotide or deoxyribonucleotide polymerization reaction.

In accordance with the present invention, the hybridizing portion of each oligonucleotide of the plurality of oligonucleotides (mixture of oligonucleotide) may be substantially different from one another (in terms of nucleic acid composition and/or length, etc.).

Further in accordance with the present invention, the first sequence tag of each oligonucleotide may be identical or substantially identical to one another (e.g., from about 80 to 100% sequence identity, from about 90 to 100% sequence identity, from about 95 to 100% sequence identity).

Additionally, in accordance with the present invention, the first sequence tag of each oligonucleotide may be substantially different from one another (in terms of nucleic acid composition and/or length, etc.).

It is to be understood herein that the term "a random sequence" refers to a sequence selected amongst a population of (random) sequences which have been isolated or synthesized in such a manner that each of the four bases (modified or not) are represented at every position in the population. Of course, once a random sequence is isolated from the population (plurality, library) of random sequences, the identity of the selected "random sequence" may be known. More particularly, the definition of "random sequence" encompasses a sequence made by randomization of nucleotides. In a particular embodiment of the present invention, the oligonucleotide may be made, for example, from deoxyribonucleic acid (deoxyribonucleotides).

In accordance with the present invention, the target nucleic acid molecule may comprise, for example DNA, such as a single-stranded DNA molecule. For instance, the single-stranded DNA molecule may be a positive strand DNA molecule or a negative strand DNA molecule. It is to be understood herein that the negative strand DNA molecule may be, for example, a complementary DNA (cDNA).

Further in accordance with the present invention, the target nucleic acid molecule may comprise, for example, RNA, such as for example, a messenger RNA or a portion thereof or an antisense RNA or portion thereof.

It is to be understood herein that the target nucleic acid(s) may comprise an unknown sequence or a known sequence. When, a target nucleic comprises a known sequence, the first oligonucleotides used to carry out methods of the present invention may be defined to be complementary to a desired known sequence of the target. Alternatively, when the target nucleic acid(s) comprises an unknown sequence, the first oligonucleotides used to carry out the method of the present invention may be a plurality of first oligonucleotides which may each comprise a random sequence. It is to be understood herein that at least one random sequence of at least one oligonucleotide may hybridize to the target in such a way that the 5'-overhanging portion (sequence tag) may be used as a template for a DNA polymerase and the 3'-end of the target may be used as a primer extension site for the DNA polymerase.

Thus, a first or second oligonucleotide may hybridize to the 3'-end of a target nucleic acid (or first template) (through the hybridizing portion of the oligonucleotide) in such a manner that the 5'-overhanging portion remains non-hybridized and extends past the extreme 3'-end of the target, the DNA polymerase enzyme may use the 5'-overhanging portion (comprising a sequence tag) as a template and the 3'-end of the target as a primer extension site. When the 3'-end of the oligonucleotide is blocked, the oligonucleotide may not serve as a site for primer extension by the DNA polymerase.

For example, and in accordance with one embodiment of the present invention, a terminal sequence tag may be added to an unknown target nucleic acid molecule (e.g., single species or multiple species) by contacting a sample containing the unknown target nucleic acid with a mixture of first oligonucleotides (i.e., a library of first oligonucleotides) each comprising a first sequence tag and a random sequence under conditions allowing hybridization of the target and first oligonucleotides and extending the target using the first sequence tag portion of the first oligonucleotides as template.

Each of the random sequences comprised within the first oligonucleotides may be the same or different (the plurality of first oligonucleotides may thus represent a library of random sequences attached to a first sequence tag of invariable or low variability (e.g., 0 to 20% sequence variation amongst first tag sequence of each of the first oligonucleotides).

In a further embodiment of the present invention, the terminal tagging of unique species of target nucleic acid having a known nucleic acid sequence may thus be made by contacting a sample (e.g., a solution, tissue, etc.) containing the target nucleic acid with a first oligonucleotide which may include a first portion comprising a first tag sequence and a second portion selected from the group consisting of a random sequence or a sequence substantially complementary to a corresponding portion located at a 3'-end of the target nucleic acid molecule under conditions allowing hybridization of the target with the first oligonucleotide and extending the target using the sequence tag portion of the first oligonucleotide as template.

In an alternative embodiment of the present invention, the terminal tagging of unique species of a target nucleic acid having an unknown nucleic acid sequence may be made by contacting a sample (e.g., a solution, tissue, etc.) containing the target nucleic acid with a first oligonucleotide which may include a first portion comprising a first tag sequence and a second portion comprising a random sequence under conditions allowing hybridization of the target and first oligonucleotides and extending the target using the sequence tag portion of the first oligonucleotides as template. In order to augment the chances of tagging the known target nucleic acid, a mixture of first oligonucleotides comprising a library of random sequences attached to the first tag sequence may be used.

In a further alternative embodiment, the terminal tagging of multiple target nucleic acid species having known nucleic acid sequence may be made by contacting a sample (e.g., a solution, tissue, etc.) containing the multiple target nucleic acid species with a mixture of first oligonucleotides each of which may include a first portion comprising a first tag sequence and a second portion selected from the group consisting of a random sequence or a sequence substantially complementary to a corresponding portion located at a 3' end of said target nucleic acid molecule under conditions allowing hybridization of the target with the first oligonucleotides and extending the target using the sequence tag portion of the first oligonucleotides as template.

In accordance with the present invention, the second portion of the first oligonucleotide may be different for each oligonucleotide whereas the first portion may be substantially identical for each oligonucleotide.

In yet a further alternative embodiment of the present invention, the terminal tagging of multiple nucleic acid species having an unknown nucleic acid sequence may be made by contacting a sample (e.g., a solution, tissue, etc.) containing the nucleic acid with a mixture of first oligonucleotides each of which may include a first portion comprising a first tag sequence and a second portion comprising a random sequence under conditions allowing hybridization of the target with the first oligonucleotides and extending the target using the sequence tag portion of the first oligonucleotides as template.

It is to be understood herein that several sequence tag may be added to the terminal end of nucleic acid molecules by repeating one or more steps of the method of the present invention.

In accordance with the present invention, the first sequence tag may comprise a nucleic acid sequence which may be selected, for example, from the group consisting of a promoter sequence, an endonuclease restriction site, an hybridization site and combination thereof and/or any sequence of interest.

The oligonucleotides and target nucleic acid molecules may be allowed to anneal by heating a mixture of these two components at an elevated temperature (e.g., greater than about 37° C.) for a period of time and then incubating at a temperature that is desirable for enzymatic extension of the nucleic acid molecules, for example by a DNA Polymerase. The desirable temperature and other enzymatic conditions are determined based on the characteristics of the enzyme used for the reaction and guidance for such conditions is provided by the manufacturer or is known in the art. The target nucleic acid molecules may therefore, be extended by using a DNA polymerase, which may be any enzyme capable of synthesizing DNA by extending a DNA or RNA primer using a DNA or RNA template. The DNA polymerase may be (substantially) free of exonuclease activities, either 3' to 5' or 5' to 3' although not necessarily. Preparations containing the DNA polymerase may be substantially free of agents capable of nucleic acid hydrolysis. Examples of DNA polymerase which may be used include, without limitation, [Klenow exo⁻DNA polymerase, Bst DNA polymerase, AMV and M-MLV reverse transcriptases etc.

As indicated above, the DNA polymerase reaction therefore may comprise the desirable concentrations of cofactors and deoxynucleoside triphosphates for DNA synthesis using the particular DNA polymerase and may be performed under the conditions of pH, ionic strength and temperature that are desirable for the enzyme that is used. Such reaction conditions are known to those skilled in the art. The reaction is performed for a sufficient period of time to allow extension of the nucleic acid molecules using the oligonucleotides as template. The reaction may be terminated using any chemical, enzymatic, mechanical or thermal methods, and the extended nucleic acid molecules may be purified from the unused oligonucleotides using size exclusion or any other suitable separation method known in the art. The resulting nucleic acid molecules have a terminal sequence tag that is complementary to the sequence tag contained in the oligonucleotide The present invention also relates to the addition of a second sequence tag to a target nucleic acid or to a first template. The second sequence tag may comprise any sequence of interest as well as multiple sequence of interest. Exemplary sequence of interest may include, for example, a promoter, an endonuclease restriction site, etc.

The present invention thus also relates to a method for adding a second sequence tag to a target nucleic acid or to a first template comprising a complementary first sequence tag described herein, the method may comprise the steps of;
  i) contacting the first template with a second oligonucleotide which may comprise a) a 5'-overhanging portion which may include the second sequence tag (a sequence of interest); and b) an hybridizing portion which may comprise a first sequence tag or a portion of a first sequence tag and substantially identical sequences (80 to 100% identity with first sequence tag or fragments thereof
  the contacting step may be effected, for example under conditions allowing hybridization of the hybridizing portion with the first template and;
  ii) extending wholly or partially the first template and second oligonucleotide to generate a second template.

The present invention also relates to the addition of a second sequence tag to a plurality of target nucleic acids or to a plurality of first templates comprising a complementary first sequence tag.

Therefore, the present invention also relates to a method which may comprise the steps of;
  i) contacting the plurality of first templates with a plurality of second oligonucleotides each of the second oligonucleotides may comprise; a) a 5'-overhanging portion which may include the second sequence tag (a sequence of interest); and b) an hybridizing portion which may comprise a first sequence tag or a portion of a first sequence tag or substantially identical sequences (80 to 100% identity with first sequence tag or portion thereof) under conditions which may allow hybridization of the hybridizing portion with the plurality of first templates and;
  ii) extending wholly or partially the plurality of first templates and second oligonucleotides to generate a second template.

It is to be understood herein that the first sequence tag comprised in the first oligonucleotide may be identical or substantially identical (e.g., 80-100% sequence identity over the entire sequence or over a portion of the sequence) to the first sequence tag or a portion of a first sequence tag of the second oligonucleotide. The second oligonucleotide may thus anneal to the totality or to portion of complementary first sequence tag. In accordance with the present invention, the first sequence tag of each second oligonucleotide may alternatively be identical to one another.

It is also to be understood herein that the 5'-overhanging portion of the second and first oligonucleotide may be different from one another of alternatively may be substantially identical (80-100% sequence identity) to one another.

In accordance with the present invention, the hybridizing portion may be able to hybridize at the 3'-end (extreme 3'-end) of the first template and the 5'-overhanging portion may serve as a template for a ribonucleotide or deoxyribonucleotide polymerization reaction. In accordance with the present invention, the 3'-end of the first template may serve as a primer extension site for a DNA polymerase.

Further in accordance with the present invention, the firs, second or both oligonucleotides may be made of ribo- or deoxyribonucleic acid or combination thereof.

Also in accordance with the present invention, the first template and second template may comprise DNA or RNA.

Therefore it is to be understood herein that the second template may be at least partially double-stranded or totally double-stranded. For example, the second template may be double-stranded in the promoter region and the remaining may be single-stranded.

Alternatively, the second template may comprise a double-stranded second sequence tag region such as for example, a double-stranded promoter region, a double-stranded restriction endonuclease region etc.

In accordance with the present invention, the double-stranded promoter region may comprise, for example, a double-stranded RNA polymerase promoter.

In accordance with the present invention, the double-stranded promoter may be located at a 5'-end or 3'-end of a first or second template.

In an embodiment of the present invention, the second sequence tag (sequence of interest) may be selected from the group consisting of a promoter sequence, an endonuclease restriction site, an hybridization site and combination thereof and/or any other sequence of interest.

As indicated above, a RNA polymerase promoter sequence may be added to a target DNA molecule by forming, for example, a first DNA template as described herein and forming a second DNA template having a double-stranded RNA polymerase promoter sequence (see schematic of FIG. 4 for illustration). The remaining of the second DNA template may be double-stranded or not.

In accordance with the present invention, the first, second or both oligonucleotides may be composed in part of nucleotides other than deoxyribonucleotides provided that they may still function as template for DNA polymerization.

The reaction may thus comprise the first DNA template, the second oligonucleotide, a DNA polymerase, deoxyribonucleoside triphosphates and the appropriate reaction buffer as described herein.

The reaction may be allowed to proceed at selected temperatures and for sufficient time to enable the first template (DNA template or RNA template) and the second oligonucleotide (though the hybridizing portion) to anneal and the 3'-end of the first template. The first template may be extended with the second oligonucleotide serving as the template and the 3'-end of the first template as primer extension. Extension of the second oligonucleotide may also proceed concomitantly.

The present invention more particularly relates to a method for adding a terminal sequence tag to a target nucleic acid molecule, the method may comprise the step of;
 a. contacting the target nucleic acid molecule with a first oligonucleotide which may comprise; a) a first 5'-overhanging portion which comprise a first sequence tag; b) a first hybridizing portion which may be able to hybridize to the target nucleic acid molecule, and; c) a blocked 3'-end, under conditions which may allow hybridization of the first hybridizing portion with the target nucleic acid molecule,
 b. extending the target nucleic acid molecule to generate a first template which may comprise a complementary first sequence tag,
 c. contacting the first template with a second oligonucleotide which may comprise; a) a second 5'-overhanging portion which may comprise a second sequence tag; and b) a second hybridizing portion which may comprise a first sequence tag,
  under conditions which may allow hybridization of the second hybridizing portion with the first template, and;
 d. extending wholly or partially the first template and second oligonucleotide to generate a second template.

The present invention also more particularly relates to a method for adding a terminal sequence tag to a plurality of target nucleic acid molecules, the method may comprise, for example;
 a. contacting the plurality of target nucleic acid molecules with a plurality of first oligonucleotides each may comprise; a) a first 5'-overhanging portion which may comprise a first sequence tag; b) a first hybridizing portion which may be able to hybridize to the plurality of target nucleic acid molecules, and; c) a blocked 3'-end,
  under conditions which may allow hybridization of the first hybridizing portion with the plurality of target nucleic acid molecules,
 b. extending the plurality of target nucleic acid molecules to generate a plurality of first templates which may comprise a complementary first sequence tag,
 c. contacting the plurality of first templates with a (a mixture of) second oligonucleotides which may comprise a) a second 5'-overhanging portion which may comprise a second sequence tag; and b) a second hybridizing portion which may comprise a first sequence tag, under conditions which may allow hybridization of the second hybridizing portion with the plurality of first templates and;
 d. extending wholly or partially the plurality of first templates and second oligonucleotides to generate a plurality of second templates.

When the target nucleic acid molecule is a sense RNA (e.g., mRNA), the RNA may be converted into a cDNA prior to performing methods of the present invention. Therefore the methods of the present invention further comprise a step of converting a mRNA into a (complete or partial) cDNA prior to adding a (terminal) sequence tag.

In accordance, with the present invention, a step of removing or inactivating the first oligonucleotide (or plurality of first oligonucleotides) before contacting the first template with a second oligonucleotide may also be performed.

In accordance with the present invention, the first and second 5'-overhanging portion may be identical or different.

It is to be understood that the method of the present invention may "comprise" the indicated steps or may "consist essentially" of the indicated steps or even may "consist" of the indicated steps.

As used herein the term "consisting essentially of" means that the method consists of the indicated steps and comprises other steps which does not affect in a significant manner, the working of the methods.

Methods for adding first, second or first and second sequence tag to a target nucleic acid molecule are thus encompassed by the present invention.

One advantage of the methods of the present invention is that it may allow, for example, terminal tagging of nucleic acids molecules such as a full length cDNA. The sequence tag which is introduced may be used as a primer binding site for subsequent amplification of the DNA molecule and/or sequencing of the DNA molecule and therefore provides means for identification and cloning of the 5'-end or the complete sequence of previously unknown mRNAs sequence.

When the sequence tag introduced by the method of the present invention is a RNA polymerase promoter or comprise a RNA polymerase promoter, linear amplification of RNA from tagged cDNA may therefore occur and permits quantification of the relative abundance of the initial target (e.g., mRNA) in a sample.

The addition of a tag at the 5'-end of a nucleic acid may also be advantageous in the generation of full length or partial cDNA libraries and therefore allows identification of the complete or partial sequence of RNA species or differentially expressed RNA species.

Exemplary Embodiments of Methods for Transcribing RNA from First or Second Template Having a Double-Stranded Promoter The present invention additionally provides methods for generating RNA from the template described herein.

The method may comprise, for example, providing the first template to which an oligonucleotide comprising a RNA polymerase promoter is annealed, with a RNA polymerase enzyme and RNA polymerase reagents under condition suitable for RNA polymerization. It is to be understood herein that a first template may be suitable for RNA transcription if an oligonucleotide comprising a RNA polymerase promoter has been annealed to it, thus making a double-stranded RNA polymerase promoter.

The method may also comprise, for example, providing the second template comprising a double-stranded RNA polymerase promoter (and other regulatory regions) with a RNA polymerase enzyme and RNA polymerase reagents under condition suitable for RNA polymerization.

When the target nucleic acid is, for example, a single-stranded positive DNA strand, the method described herein may generate a first DNA template and a second DNA template which may have, for example, a double-stranded RNA polymerase promoter located at a 3'-end of the double-stranded second DNA template (which is at least partially or totally double-stranded, or at least double-stranded in the promoter region), thereby producing an antisense RNA using the method of generating RNA described herein.

When the target nucleic acid is, for example, a single-stranded negative DNA strand, the method described herein may generate a first DNA template and a second DNA template which may have, for example, a double-stranded RNA polymerase promoter located at a 5'-end of the double-stranded second DNA template (which is at least partially or totally double-stranded, or at least double-stranded in the promoter region), thereby producing a sense RNA using the method of generating RNA described herein.

The present invention relates in an additional aspect thereof, to a method for generating RNA from a nucleic acid comprising a suitable second template (i.e., comprising a RNA polymerase promoter) as described herein, the method may comprise providing the nucleic acid with a RNA polymerase enzyme and RNA polymerase reagents under condition suitable for RNA polymerization.

The present invention also relates to a method for generating RNA from a vector described herein, the method may comprise providing the vector with a RNA polymerase enzyme and RNA polymerase reagents under condition suitable for RNA polymerization.

Additionally, the present invention relates to a method for generating RNA from a cell as described herein, the method may comprise providing the cell with a RNA polymerase enzyme and RNA polymerase reagents under condition suitable for RNA polymerization.

In an embodiment of the present invention, the nucleic acid target used in the method of the present invention may be a single-stranded positive DNA molecule thereby introducing a double-stranded RNA polymerase promoter at a region located at a 3'-end of the second template.

In a further embodiment of the present invention, the nucleic acid target used in the method of the present invention, may be a single-stranded negative DNA or a cDNA molecule thereby introducing a double-stranded RNA polymerase promoter at a region located at a 5'-end of the second template.

In yet a further embodiment of the present invention, the nucleic acid target used in the method of the present invention may be a sense RNA molecule thereby introducing a double-stranded RNA polymerase promoter at a region located at a 3'-end of the second template.

In accordance with the present invention, the nucleic acid target used in the method of the present invention may be an anti-sense RNA molecule thereby introducing a double-stranded RNA polymerase promoter at a region located at a 5'-end of the second template.

As described herein, the RNA polymerase suitable for the methods of the present invention may be any enzyme capable of recognizing the double-stranded promoter and specifically initiating RNA synthesis at the defined initiation site within close proximity to the promoter. Preparations comprising the RNA polymerase may be relatively free of contaminating agents with DNase or RNase activities. In addition the RNA polymerase may be capable of synthesizing several copies of RNA per functional copy of DNA template in a desirable period of time. In accordance with the present invention, the RNA polymerase may be selected from the group consisting of, and without limitation, the bacteriophage T7 RNA polymerase, the phage T3 RNA polymerase, the *Salmonella* phage sp6 RNA polymerase etc. It is understood by those skilled in the art that the use of alternative RNA polymerases will involve changes to the sequence of the promoter template according to the specificity of the particular RNA polymerase.

The transcription reaction may comprise the desirable concentrations of cofactors and nucleoside triphosphates for RNA synthesis using the particular RNA polymerase. The transcription reaction may be performed under the conditions of pH, ionic strength and temperature that are desirable for the enzyme which is used. Such reaction conditions are known to those skilled in the art and are usually provided by the manufacturer.

RNA may thus be synthesized from the second DNA template comprising a double-stranded RNA polymerase promoter sequence generated by the method of the present invention. Therefore, RNA may be synthesized from the second DNA template having a double-stranded promoter sequence.

It is to be understood herein that even when the remaining of the first or second DNA template is not double-stranded, RNA synthesis may occur to the extent that at least the RNA polymerase region is double-stranded. It is therefore understood herein that RNA may be synthesized from a template having a double stranded promoter sequence and a single- or double-stranded remaining sequence.

According to a present embodiment, RNA may be synthesized from the first or second DNA template having a double-stranded promoter sequence by using an RNA polymerase that is specific to the particular promoter sequence. The reaction may comprise, for example, the DNA templates (e.g., first DNA template having a double-stranded promoter sequence or second DNA template having a double-stranded promoter), a RNA polymerase buffer [40 mM Tris-HCl (pH 7.9), 6 mM $MgCl_2$, 2 mM spermidine, 10 mM DTT] supplemented with an equimolar mixture of ATP, UTP, GTP and CTP incubated at about 37° C. for a specified period.

The method described herein allows for a linear amplification of known or unknown target nucleic acid molecules and are thus suitable for quantification of the relative abundance of such target.

It is to be understood herein that the RNA produced by the method of the present invention may further be reverse transcribed and/or amplified to generate, for example, cDNA libraries.

Another aspect of the invention provides a method for synthesizing RNA from DNA molecules. This method comprises forming first DNA templates by adding a terminal sequence tag to the DNA molecules; forming first DNA templates having a double-stranded promoter sequence and/or forming second DNA templates which may be at least double-stranded in the promoter region and synthesizing RNA from the first or second DNA templates having a double-stranded promoter sequence.

In a particular implementation of this aspect of the invention, the first DNA templates having a double-stranded promoter sequence may be formed by contacting the first DNA templates with oligonucleotides containing the sequence tag, a promoter template, a random sequence and a blocked 3' terminus, under conditions such that, the random sequence anneals with the DNA molecules and the DNA molecules are extended using the sequence tag and promoter as template.

In a particular implementation of this aspect, the second DNA templates having a double-stranded promoter sequence may be formed by contacting the first DNA templates without a promoter with a second oligonucleotide containing the sequence tag complement to the tag sequence contained in the first DNA templates and a promoter sequence template, under conditions such that, the first DNA templates anneal with the sequence tag complement of the second oligonucleotide and are extended using the promoter sequence as template. In a particular implementation of this aspect, the second oligonucleotide may contain a blocked 3' terminus.

In a particular implementation of this aspect, a terminal sequence tag may be added to DNA molecules by contacting with a mixture of oligonucleotides, each having a sequence tag, a random sequence and a blocked 3' terminus, under conditions such that, the random sequence anneals with the DNA molecules and the DNA molecules are extended using the sequence tag as template. In a particular implementation of this aspect, DNA molecules may be formed by contacting a mixture containing mRNA with a primer having a terminal sequence complementary to the mRNA, under conditions such that, the terminal sequence of the primer anneals with the mRNA and is extended using the mRNA as template.

Another aspect of the invention provides a method for synthesizing first RNA templates having a double-stranded promoter sequence comprising contacting the RNA molecules with oligonucleotides containing the sequence tag, a promoter template, a random sequence and a blocked 3' terminus, under conditions such that, the random sequence anneals with the RNA molecules and the RNA molecules are extended using the sequence tag and promoter templates as template.

In a particular implementation of this aspect, the second RNA templates having a double-stranded promoter sequence may be formed by contacting the first RNA templates without a promoter with a second oligonucleotide containing the sequence tag complement to the tag sequence contained in the first RNA templates and a promoter sequence template, under conditions such that, the first RNA templates anneal with the sequence tag complement of the second oligonucleotide and are extended using the promoter sequence as template.

In a particular implementation of this aspect, the second oligonucleotide may contain a blocked 3' terminus. In a particular implementation of this aspect, a terminal sequence tag may be added to DNA molecules by contacting with a mixture of oligonucleotides, each having a sequence tag, a random sequence and a blocked 3' terminus, under conditions such that, the random sequence anneals with the DNA molecules and the DNA molecules are extended using the sequence tag as template. In a particular implementation of this aspect, DNA molecules may be formed by contacting a mixture containing mRNA with a primer having a terminal sequence complementary to the mRNA, under conditions such that, the terminal sequence of the primer anneals with the mRNA and is extended using the mRNA as template.

Exemplary Embodiments of Methods for Amplifying Templates and Identification of Target Nucleic Acids DNA sequences may be amplified using standard techniques which are known by those of skill in the art.

The first or second template (partially or wholly double-stranded) generated by the methods of the present invention may thus be amplified by using at least one primer which is complementary to a sequence contained in the template. One of the sequence which may serve as a primer binding site is, for example, a sequence tag introduced by the method of the present invention.

DNA templates may be amplified in vitro using, for example, technologies such as PCR, NASBA and SDA. The primers may contain, for example, a restriction endonuclease site in order to aid in cloning of the amplified DNA templates.

As will become apparent from the above methods, when the sequence tag is introduced in a full length cDNA generated by reverse transcription of an unknown mRNA, this tag (tag site) may subsequently be used for amplification, sequencing, transcription (transcription-coupled translation) and therefore identification of the complete sequence of the unknown target nucleic acid as well as its amino acid sequence.

Alternatively, when a sequence tag is introduced in a full length cDNA generated by reverse transcription of a partially known mRNA, this tag (tag site) may subsequently be used to isolate and identify the complete sequence of the target nucleic acid molecule.

Therefore, another aspect of the invention provides a method for amplifying terminal sequences of DNA molecules comprising: forming first DNA templates by adding a terminal sequence tag to the DNA molecules; forming double-stranded DNA templates by extending a first primer; and amplifying the DNA templates by extending the first primer and a second primer. According to this embodiment the double-stranded DNA templates may be formed by contacting the first DNA templates with a first primer having a sequence complementary to the sequence tag, under conditions such that, the sequence of the primer anneals with the sequence tag of the first DNA templates and is extended. In a particular implementation of this aspect, the DNA templates may be amplified by contacting with the first primer and a second primer containing a sequence complementary to a sequence from the complementary DNA strand to the first DNA templates, under conditions such that the primers anneal to complementary templates and are extended. In a particular implementation of this aspect, a terminal sequence tag may be added to DNA molecules by contacting with a mixture of oligonucleotides, each having a sequence tag, a random sequence and a blocked 3' terminus, under conditions such that, the random sequence anneals with the DNA molecules and the DNA molecules are extended using the sequence tag as template. In a particular implementation of this aspect, DNA molecules may be formed by contacting a mixture containing mRNA with a primer having a terminal sequence complementary to the mRNA, under conditions such that, the terminal sequence of the primer anneals with the mRNA and is extended using the mRNA as template.

Exemplary Embodiments of Kits and Reagents

The present invention also relates to kits and reagents for carrying out the present invention.

The present invention therefore relates in one aspect thereof to a first template and second template generated by the methods described herein as well as the RNA generated by their transcription.

In accordance with the present invention, the second template may be at least partially double-stranded or totally double-stranded.

Further in accordance with the present invention, the second template may comprise a double-stranded second sequence tag region. The double-stranded second sequence tag region may be, for example, a double-stranded promoter region, a double-stranded restriction endonuclease region, etc.

In accordance with the present invention, the double-stranded promoter region may comprise, for example, a double-stranded RNA polymerase promoter.

In additional aspects, the present invention relates to a nucleic acid molecule comprising a first template or a second template generated by the methods described herein.

In further aspects, the present invention relates to a vector comprising a first template or a second template generated by the methods described herein.

In additional aspects, the present invention relates to a cell (e.g., an isolated cells, a cell line, such as, for example, a mammalian cell, an insect cell, an animal cell, etc.) which may comprise the first template, second template, nucleic acid or vector described herein.

The present invention also relates to various kits that may be used in order to perform the various methods of the present invention. Examples of kits include one or more reagents used in the methods described herein. Exemplary embodiments of kits are those which may include, for example, a container comprising at least one oligonucleotide described herein. A kit may include, for example, an oligonucleotide having a promoter sequence. A kit may also include one or more enzymes for polymerizing ribonucleotides and/or deoxyribonucleotides, such as a DNA polymerase, RNA polymerase, a reverse transcriptase. A kit may also comprise an oligonucleotide complementary to mRNA molecules (e.g., oligo(dT), or containing a specific complementary sequence).

The present invention therefore relates in one aspect thereof to a kit which may comprise a first oligonucleotide or the plurality of first oligonucleotides described herein. The kit may also further comprise a second oligonucleotide as described herein.

The present invention also relates to a kit which may comprise a second oligonucleotide as described herein.

The present invention relates more particularly to a kit which may comprise: (a) a first oligonucleotide as described herein (b) a DNA polymerase and reagents for extending the 3'-ends of the nucleic acid molecules; (c) size selection columns and buffers for removal of unused first oligonucleotide; and (d) instructions for hybridizing the first oligonucleotide to the target nucleic molecule, extending the target nucleic acid molecule with the DNA polymerase using the first oligonucleotide as template, and creating first DNA or RNA templates with, for example, double-stranded regions.

In accordance with the present invention, the kit may further comprise a second oligonucleotide as described herein and instructions to use the second oligonucleotide as template to form second DNA templates or second RNA templates, containing a sequence of interest such as, for example, a promoter.

In accordance with the present invention, the kit may further comprise a reverse transcriptase, at least one enzyme for RNA hydrolysis and an oligonucleotide complementary to mRNA molecules (e.g., oligo(dT)).

Further in accordance with the present invention, the kit may further comprise a RNA polymerase matching a functional promoter and reagents, and cofactors for in vitro RNA synthesis from the promoter.

Also in accordance with the present invention, the kit may further comprise a first primer which may correspond to the sequence tag and at least one second primer for exponential amplification of double stranded second DNA template, wherein the primers anneal to the a strand of the template which complementary and are extended repeatedly.

Exemplary Embodiments of Compositions

In an additional aspect, the present invention relates to a composition which may comprise a target nucleic acid molecule having annealed at its 3'-end thereof a first oligonucleotide which may comprise a) a 5'-overhanging portion substantially non-hybridized to the target nucleic acid molecule, the 5'-overhanging portion may comprise a sequence tag; b) an hybridizing portion hybridized to the target nucleic acid molecule, and; c) a blocked 3'-end or an unblocked 3'-end.

In accordance with the present invention, the nucleic acid molecule may be DNA or a RNA or a DNA/RNA hybrid, etc.

In accordance with the present invention, the sequence tag may be a promoter sequence.

The present invention relates in one aspect thereof, to methods kits and reagents as described in U.S. patent application Ser. No. 11/000,958 published on Jul. 14, 2005 under No. US 2003/0153333 A1.

The present invention also relates to improvements to the methods, kits and reagents described above.

Exemplary Embodiments of Improvements to the Methods

More particularly, the present methods, kits and reagents have been improved herewith by using modified oligonucleotide and by reducing the number of steps.

The present invention relates in an aspect therefore to an oligonucleotide which may comprises, for example, a) a 5'-overhanging portion which may comprise a first sequence tag; b) an hybridizing portion which may be able to hybridize to the target nucleic acid molecule, the hybridizing portion may comprise a ribonucleic acid section; and c) a blocked 3'-end.

The present invention also relates to a kit comprising an oligonucleotide as described herein. The kit may further comprise an enzyme and/or one or more other reagents or instructions useful to carry out the method of the present invention.

The present invention relates in an additional aspect thereof, to a method for adding a terminal sequence tag to a target nucleic acid molecule, the method may comprise, for example,
- i. contacting the target nucleic acid molecule with an oligonucleotide which may comprise: a) a 5'-overhanging portion which include a first sequence tag; b) an hybridizing portion which may be able to hybridize to the target nucleic acid molecule, the hybridizing portion may comprise a ribonucleic acid section and; c) a blocked 3'-end, under conditions which may allow hybridization of the hybridizing portion with the target nucleic acid molecule,
- ii. extending the target nucleic acid molecule to generate a first template which may comprise a complementary first sequence tag,
- iii. removing (e.g., enzymatically removing) the ribonucleic acid section of the oligonucleotide to generate a primer extension site and;
- iv. extending the oligonucleotide to generate a second template.

The present invention also relates in a further aspect to a method for adding a terminal sequence tag to a plurality of target nucleic acid molecules, the method may comprise, for example,
- i. contacting the plurality of nucleic acid molecules with a plurality of oligonucleotides each of which may comprise: a) a 5'-overhanging portion which may comprise a first sequence tag; b) an hybridizing portion which may be able to hybridize to a target nucleic acid molecule, the hybridizing portion may comprise a ribonucleic acid section and; c) a blocked 3'-end, under conditions which may allow hybridization of the hybridizing portion with the target nucleic acid molecule,
- ii. extending the plurality of target nucleic acid molecules to generate a plurality of first templates which may comprise a complementary first sequence tag,
- iii. removing (e.g., enzymatically removing) the ribonucleic acid section of the oligonucleotide to generate a primer extension site and;
- iv. extending the oligonucleotide to generate a plurality of second templates.

In accordance with the present invention, the first sequence tag may be selected, for example, from the group consisting of a promoter sequence, an endonuclease restriction site, an hybridization site and any combination thereof.

In accordance with the present invention, the removal step may be performed with the help of an enzyme such as, for example, a RNase.

Further in accordance with the present invention, the hybridizing portion may comprise a) a random sequence or b) a nucleic acid sequence substantially complementary (e.g., 80 to 100% complementarity over the entire sequence or portion of sequences) to a portion located at a 3'-end of a target nucleic acid molecule (with respect to the 5'->3' direction).

The hybridizing sequence of the improved oligonucleotide may thus comprise in part or as a whole, an equal representation of ribonucleotides G, A, U and C to form DNA:RNA composites. Wobble bases such as inosine (I) may also be used instead of standard bases at any of the positions. In addition, one or more of the ribonucleotides may be chemically modified while still maintaining a functional activity as a substrate for ribonuclease.

The replacement of part deoxyribonucleotides with ribonucleotides in the oligonucleotide is not limited to only the random sequence or 3'-complementary sequence and may include any number of nucleotides 5' and 3' of these sequences. This modification of the oligonucleotides sequence tag may facilitate the synthesis of fully double-stranded "second DNA templates" without the need for use of a second oligonucleotide containing a promoter as described above.

In addition, this improvement provides for a more homogenous terminal tagging process with the elimination of a nucleic acids clean-up step. As for the above-described method, the 3'-proximal random sequence may be any number of nucleotides in length but preferably between 4 and 9 (or 4 to 15). Also, the 3' terminus of the modified oligonucleotides may be chemically blocked as described in the EXAMPLE section.

According to the improved methods, reaction conditions may be applied such that, the random sequences of the oligonucleotides may anneal with the nucleic acid molecules and the nucleic acid molecules may be extended using as template the promoter containing sequence tag of the oligonucleotides.

The oligonucleotides and nucleic acid molecules may be allowed to anneal by heating a mixture of these two components at an elevated temperature (>37° C.) for a period of time and then incubating at a temperature suitable for enzymatic extension of the nucleic acid molecules, depending on the nature of the enzyme used. The nucleic acid molecules may be extended as described above by using a DNA polymerase, which may be any enzyme capable of synthesizing DNA by extending a DNA or RNA primer using either a RNA or DNA template. The DNA polymerase may be substantially free of exonuclease activities, either 3' to 5' or 5' to 3', and preparations containing the DNA polymerase may be relatively free of agents capable of nucleic acid hydrolysis. Examples of DNA polymerase that may be AMV and M-MLV reverse transcriptases, and Tth DNA polymerase.

According to an embodiment of the present invention, the nucleic acid molecules may be composed of DNA. The resulting "first DNA templates" may have a 3' promoter sequence and sequence tag (plus specific sequence tag) that is complementary (at least partially complementary) to the sequence tag contained in the oligonucleotide mixture (see schematic of FIG. 9a for illustration).

Alternatively, the resulting "first DNA templates" may comprise a 3' promoter sequence which may also serve as the sequence tag (minus specific sequence tag) that is complementary to the sequence tag contained in the oligonucleotide mixture (see schematic of FIG. 9b for illustration). The resulting "first DNA templates" are now partially double-stranded comprising a double-stranded promoter sequence with the oligonucleotide template strands still blocked at the 3' terminus (see schematic of FIGS. 9a and 9b for illustration).

According to an embodiment of methods of the present invention, RNA may be synthesized from DNA molecules by forming first DNA templates having a double-stranded promoter sequence, forming second DNA templates having a double-stranded promoter sequence and synthesizing RNA from the first or second DNA templates having a double-stranded promoter sequence.

According to an embodiment of the present invention, the nucleic acid molecules may be composed of RNA, wherein the resulting "first RNA templates" have a 3' promoter sequence and sequence tag (plus specific sequence tag) that is complementary to the sequence tag contained in the oligonucleotide mixture (see schematic of FIG. 10a for illustration). Alternatively, the resulting "first RNA templates" may have a 3' promoter sequence which may also serve as the sequence tag (minus specific sequence tag) that is complementary to the sequence tag contained in the oligonucleotide mixture (see schematic of FIG. 10b for illustration). The resulting "first RNA templates" are now partially double-stranded comprising a double-stranded promoter sequence with the oligonucleotides template strands still blocked at the 3' terminus.

According to an embodiment of the present invention, completely double-stranded "second DNA templates" having a double-stranded promoter sequence may be formed by applying reaction conditions such that, the ribonucleotide random sequence of the oligonucleotides sequence tag now part of an RNA:DNA hybrid may become hydrolyzed by a specific ribonuclease such as, ribonuclease H, thereby releasing the 3' terminus blocking group. The resulting oligonucleotides sequence tag of the double-stranded promoter of the "first DNA templates" may now contain an unblocked 3' terminus with a 3' OH group capable of extension by DNA polymerization. An RNA- or DNA-directed DNA polymerase present in the reaction under the appropriate conditions may thus extend the unblocked oligonucleotides sequence tag to synthesize the completely double-stranded "second DNA templates".

According to an embodiment of the present invention, RNA may be synthesized from a DNA template having a double-stranded promoter sequence by using an RNA polymerase that is specific to the particular promoter sequence (see schematic of FIG. 11 for illustration). The reaction comprises the DNA template, a RNA polymerase buffer [40 mM Tris-HCl (pH 7.9), 6 mM $MgCl_2$, 2 mM spermidine, 10 mM DTT] supplemented with an equimolar mixture of ATP, UTP, GTP and CTP incubated at 37° C. for a specified period.

RNA synthesis from a completely double-stranded "second DNA templates" having a double-stranded promoter sequence may proceed more efficiently than double-stranded first DNA templates containing only a double-stranded promoter sequence or partially double-stranded second DNA template. The described improvement of the selective terminal tagging method involves the use of a single oligonucleotides sequence tag instead of two separate oligonucleotides for the addition of firstly, the sequence tag and secondly, the promoter sequence in order to synthesize fully double-stranded "second DNA templates".

Although the modified oligonucleotides sequence tag may hybridize at internal sites along the nucleic acids molecules and become extended following RNase H digestion and DNA polymerization, the resulting molecules will not contain a double-stranded promoter sequence required for efficient RNA synthesis and thus no RNA from these species may be generated. A second round of tagging may be performed on RNA (or cDNA when reverse transcription occurs) produced by the methods of the present invention to further amplify target nucleic acid molecules.

When modified oligonucleotides sequence tag each having a promoter sequence, a sequence tag, a random sequence and a blocked 3'-terminus are used (see schematic of FIG. 9a for illustration), the RNA synthesized from the "first or second DNA templates" may contain the specific sequence tag sequence at its 5' terminus. Whereas, when the modified oligonucleotides comprise only a promoter sequence (and no other tag), a random sequence and a blocked 3'-terminus are used for the methods of the present invention (see schematic of FIG. 9b for illustration), the RNA synthesized from the "first or second DNA templates" will not contain a specific sequence tag sequence at the 5' terminus. Therefore, the promoter sequence of the "first or second DNA templates" may itself serve as a specific sequence tag for primer-directed DNA synthesis.

The present invention also relates to templates, RNA, composition of template annealed with oligonucleotide, etc. generated using the methods of the present invention.

Definitions

It is to be understood herein that the term "sequence tag" is a general term used to refer to either a "complementary" sequence tag or a "sense" sequence tag or to both. For example, the expression "a method for adding a sequence tag", is not intended to be restricted to a specific sense and therefore refers to either a "complementary" sequence tag or a "sense" sequence tag or to both.

As used herein the term "at least one oligonucleotide" may refer to either a numerical value or to an oligonucleotide species or sequence such as in the expression "at least one oligonucleotide species".

As used herein the term "substantially non-hybridizable" means that a sequence does not hybridize with another one in a significant manner or in a manner affecting the way the invention is carried out.

A first DNA template comprising a double-stranded region able to be recognized by restriction endonuclease is referred herein as being "activated".

As used herein the terms "sequence identity" relates to (consecutive) nucleotides of a nucleotide sequence which with reference to an original nucleotide sequence. The identity may be compared over a region or over the total sequence of a nucleic acid sequence.

Thus, "identity" may be compared, for example, over a region of 3, 4, 5, 10, 19, 20 nucleotides or more (and any number there between). It is to be understood herein that gaps of non-identical nucleotides may be found between identical nucleic acids. For example, an oligonucleotide may have 100% identity with another oligonucleotide over a portion thereof. However, when the entire sequence of both oligonucleotides is compared, the two oligonucleotides may have 50% of their overall (total) sequence identical to one another.

Oligonucleotides of the present invention or portion thereof having from about 80 to 100% sequence identity or from about 90 to 100% sequence identity or from about 95 to 100% sequence identity with an original oligonucleotide are encompassed herewith.

It is known by those of skill in the art, that an oligonucleotide having from about 80% to 100% identity may function (e.g., anneal to a substantially complementary sequence) in a manner similar to an original oligonucleotide and therefore may be used in replacement of an original oligonucleotide. For example an oligonucleotide (a nucleic acid sequence) may comprise or have from about 80% to 100% identity with an original oligonucleotide over a defined region and may still work as efficiently or sufficiently to achieve tagging of a target nucleic acid molecule.

Percent identity may be determined, for example, with n algorithm GAP, BESTFIT, or FASTA in the Wisconsin Genetics Software Package Release 7.0, using default gap weights.

As used herein the terms "sequence complementarity" refers to (consecutive) nucleotides of a nucleotide sequence which are complementary to a reference (original) nucleotide sequence. The complementarity may be compared over a region or over the total sequence of a nucleic acid sequence.

Oligonucleotides of the present invention or portion thereof having from about 80 to 100% sequence complementarity or from about 90 to 100% sequence complementarity or from about 95 to 100% sequence complementarity with an original oligonucleotide are encompassed herewith. It is known by those of skill in the art, that an oligonucleotide having from about 80% to 100% complementarity with an original sequence may anneal to that sequence in a manner sufficient to carry out the methods of the present invention. For example an oligonucleotide (a nucleic acid sequence) may comprise or have from about 80% to 100% complementarity with an original oligonucleotide and may still anneal with the original sequence in a manner sufficient to achieve tagging of a target nucleic acid molecule.

As used herein the term "first template" includes a "first DNA template" and a "first RNA template".

As used herein the term "first DNA template" means a DNA molecule, such as, for example a negative (uncoding) strand (3'->5') or a positive (coding) strand (5'->3') and which comprises at its 3'-end, a sequence tag such as a complementary first sequence tag. The complementary first sequence tag contained within the "first DNA template" may be substantially complementary to the first sequence tag contained in the first oligonucleotide used in an exemplary method of the present invention (see schematic of FIG. 2 for illustration of tagging of a cDNA molecule).

As used herein the term "first RNA template" means a RNA molecule, such as, for example, a sense or anti-sense RNA and which may comprise at its 3'-end, a sequence tag. The sequence tag contained within the "first RNA template" may be a complementary first sequence tag which may be (substantially) complementary to the first sequence tag contained in the first oligonucleotide used in an exemplary method of the present invention. The first RNA templates formed by the present methods may thus comprise a composite of deoxy- and ribonucleotides (see schematic of FIG. 3 for illustration of terminal tagging of a sense RNA), which may be effected, for example, by RNA-directed DNA polymerase such as but not limited to AMV reverse transcriptase may be used.

As used herein the term "second template" includes a "second DNA template" and a "second RNA template".

As used herein the term "second DNA template" means an at least partially double-stranded DNA molecule comprising at an end thereof, a sequence tag (sequence of interest) such as a second (and in some circumstances, a first) sequence tag (see schematic of FIG. 4 for illustration of a second DNA template).

It is to be understood herein that when the "first DNA template" used in the present method is a single-stranded DNA molecule, the "second DNA template may comprise at its 5'-end (with respect to the coding sequence) and from a 5'->3' direction 1) a second sequence tag (sequence of interest) and; 2) a first sequence tag. It is also to be understood herein that when the "first DNA template" is a single-stranded coding strand of a DNA molecule, the "second DNA template may comprise at its 3'-end (with respect to the coding sequence) and from a 5'->3' direction 1) a first sequence tag and 2) second sequence tag (a sequence of interest).

As used herein the term "second RNA template" means a RNA molecule, such as, for example, a sense or anti-sense RNA which comprises at its 3'-end and from a 5'->3' direction 1) a first sequence tag and 2) second sequence tag (a sequence of interest) or a complement of a sequence of interest.

When a linear amplification of a nucleic acid is required, it is desirable to have a first primer with a blocked 3'-end. However, in some circumstances, such as for cloning purposes, a blocked 3'-end is not always necessary.

It is to be understood herein, that if a "range" or "group" of substances (e.g. amino acids), substituents" or the like is mentioned or if other types of a particular characteristic (e.g. temperature, pressure, chemical structure, time, etc.) is mentioned, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to a percentage (%) of identity of from about 80 to 100%, it is to be understood as specifically incorporating herein each and every individual %, as well as sub-range, such as for example 80%, 81%, 84.78%, 93%, 99% etc.; and similarly with respect to other parameters such as, concentrations, elements, etc. . . .

It is in particular to be understood herein that the methods of the present invention each include each and every individual steps described thereby as well as those defined as positively including particular steps or excluding particular steps or a combination thereof; for example an exclusionary definition for a method of the present invention, may read as follows: "provided that when the nucleic acid target is a mRNA, the hybridizing portion is preferably not a oligo(dT) sequence or if an oligo(dT) is used, the 3'-end is blocked, etc.

BRIEF DESCRIPTION OF THE FIGURES

The present invention will now be described, by way of example only, with reference to certain embodiments shown in the attached Figures in which:

FIG. 8 shows a plot of the hybridization signal of the probe to Cathepsin K (vs. Precursor/Osteoclast RNA ratios), quantified by scintillation counting of bands excised from the hybridized blot shown in FIG. 7B, versus the fraction of osteoclast RNA in the RNA mixture;

FIG. 9*b* is a schematic illustrating the terminal tagging of a cDNA molecule using an improved method according to an further embodiment of the present invention;

FIG. 12 panel A is a photograph of an agarose gel showing the electrophoretic profile of transcription reactions products from tagged target generated by standard and improved methods described herein, Panel B is a Northern blot of the same product, visualized with a radioactive probe.

DETAILED DESCRIPTION

While only specific combinations of the various features of the present invention have been discussed herein, it will be apparent to those of skill in the art that desired sub-sets of the disclosed features and/or alternative combinations of these features may be utilized.

Therefore, it will be apparent to those skilled in the art that various modifications and variations may be made in the apparatus and methods of the present invention without departing from the spirit or scope on the invention. Thus, it is intended that the present invention covers the modifications and variations of this invention provided they come within the scope of the appended claims and their equivalents. Additionally, the following examples are appended for the purpose of illustrating the claimed invention, and should not be construed so as to limit the scope of the claimed invention.

As discussed herewith the products obtained by the methods of the present invention may have a variety of utilities including, without limitation, cloning of known or unknown target nucleic acid molecule, the generation of hybridization probes, the construction of cDNA libraries, and the analysis and identification of the terminal sequence or complete nucleic acid sequences (and amino acid sequence) of the target nucleic acid molecules. More particularly, methods of the present invention allow linear amplification of a target nucleic acid for determination of the relative abundance of the target amongst other nucleic acid molecules.

EXAMPLE 1

Figure 1:
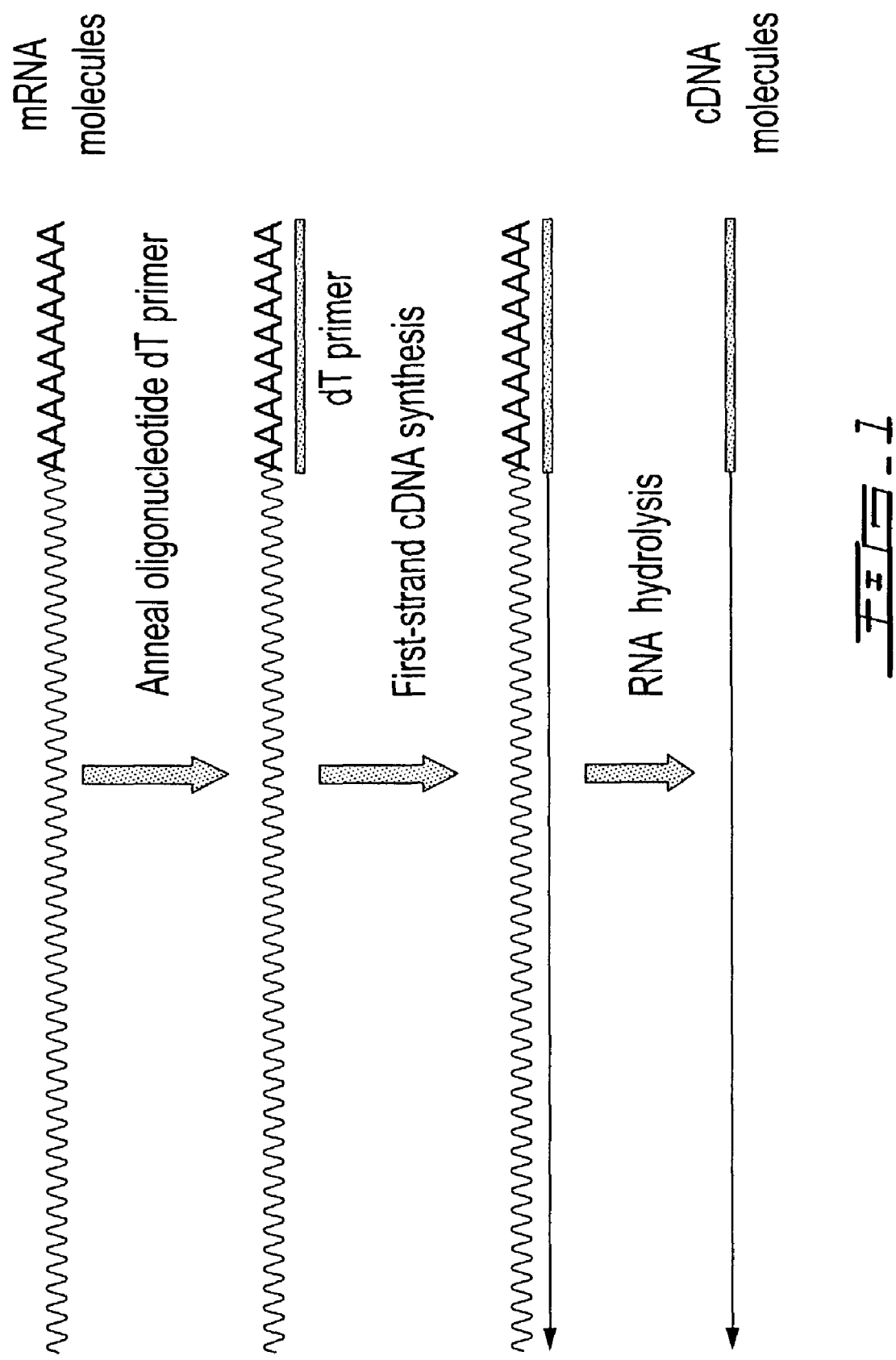
FIG. 1 shows a schematic illustration of the synthesis of cDNA molecules from mRNA molecules.

Attachment of an Oligonucleotide Sequence Tag to the Terminal 3' Ends of cDNA Molecules Total RNA from mouse brain (Ambion) was repurified using the RNeasy procedure (Qiagen). The mRNA population contained in 4 µg of total RNA was used for making first-strand cDNA in a standard cDNA synthesis reaction containing 7.5 µM oligo dT primer (Seq. ID. No. 1; $(dT)_{20}V$ (V=A, C or G) containing a 5'-Not I restriction endonuclease sequence in order to facilitate cloning), 10 mM Tris-HCl (pH 8.3), 50 mM KCl, 6 mM $MgCl_2$, 5 mM DTT, 1 mM dATP, 1 mM dGTP, 1 mM dCTP, 1 mM TTP and a reverse transcriptase in a final volume of 20 µL. The reaction was allowed to proceed for 60 minutes at the recommended incubation temperatures. The RNA templates were then removed by enzymatic digestion with RNase A and H simultaneously, and the cDNA purified and recovered in 50 µL EB buffer (Qiagen) (see schematic of FIG. 1 for illustration).

Figure 2:
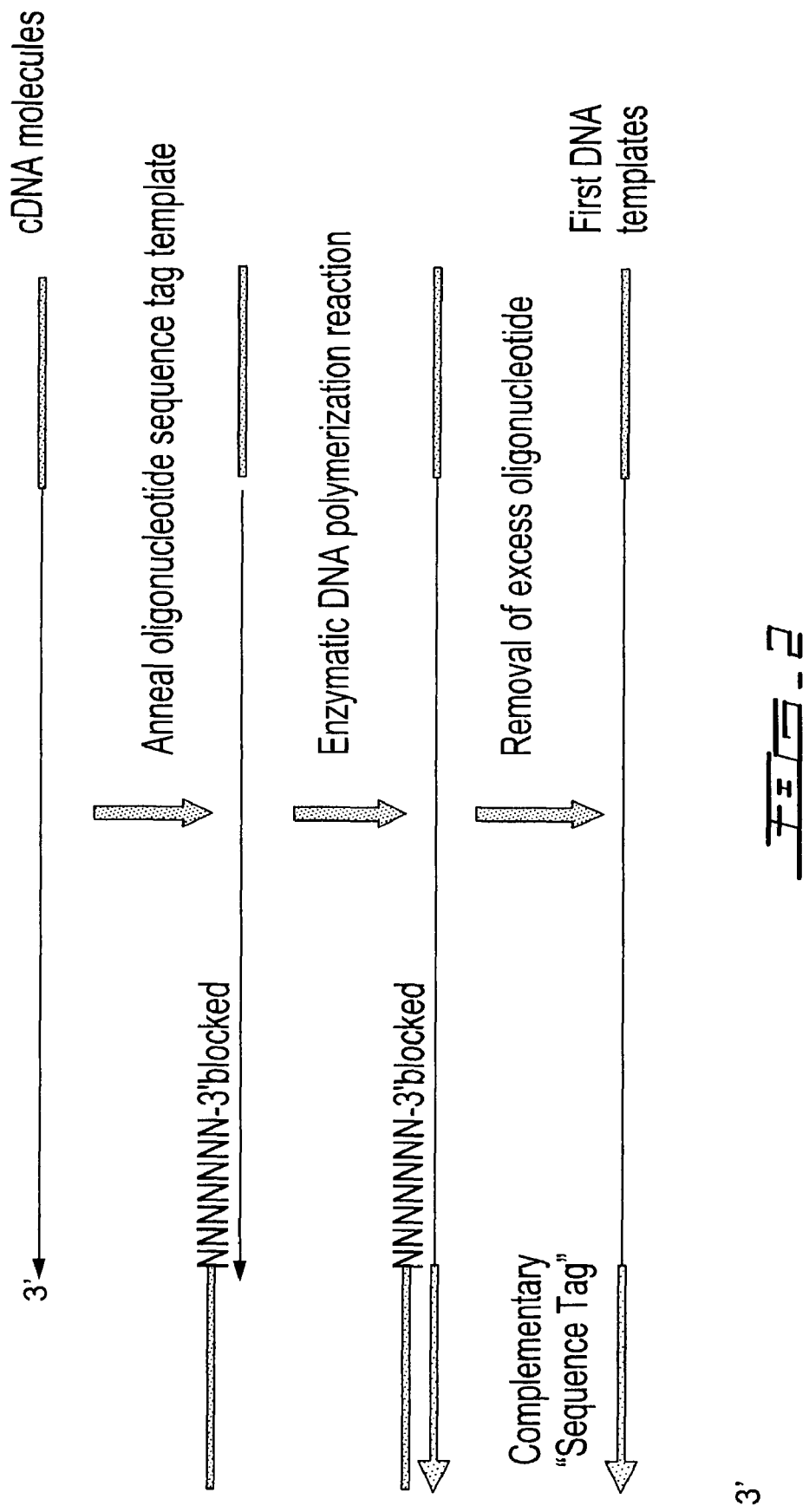
FIG. 2 shows a schematic illustration of the synthesis of first DNA templates comprising a sequence tag from cDNA molecules.
Figure 3:
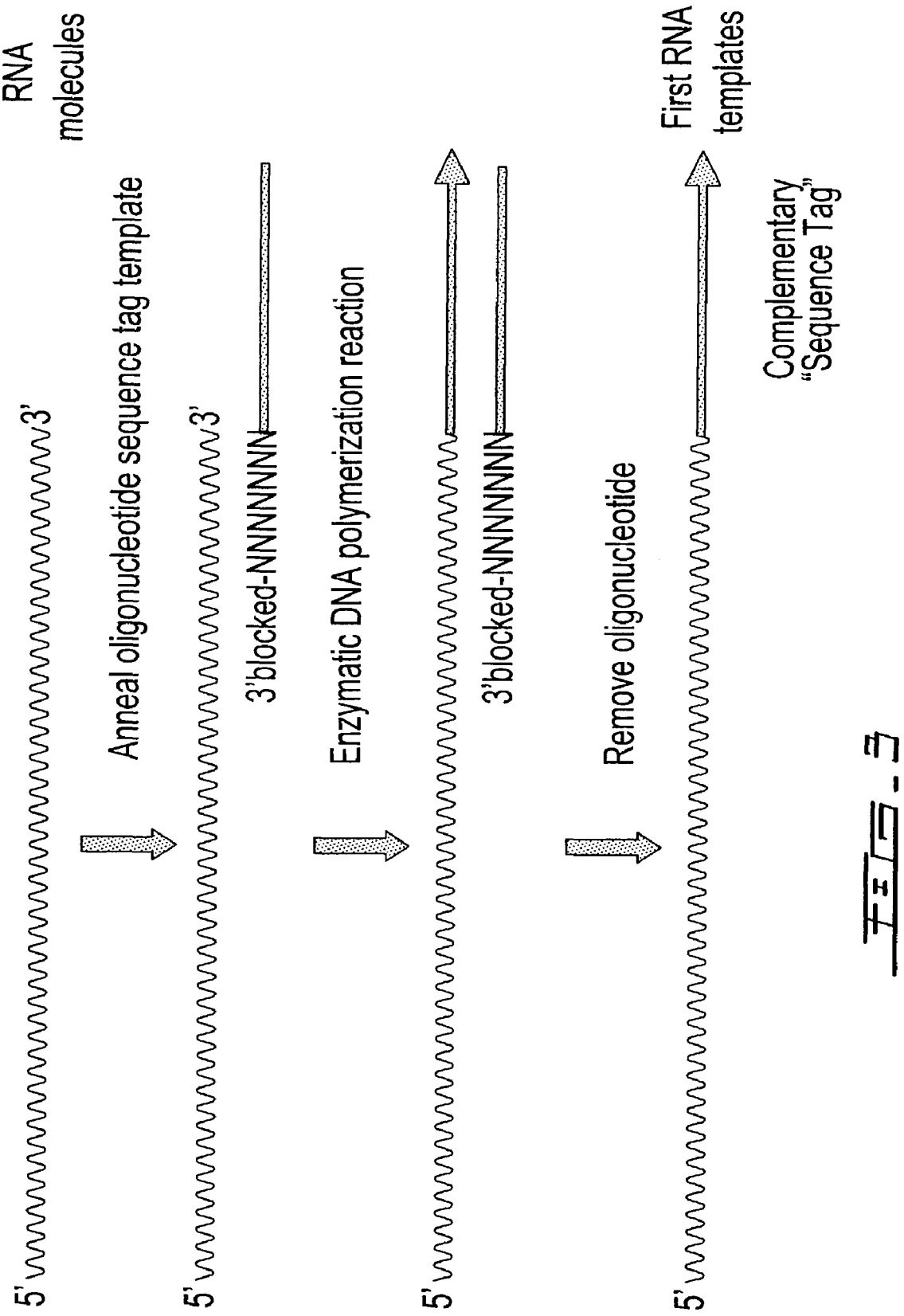
FIG. 3 shows a schematic illustration of the synthesis of first RNA templates comprising a sequence tag from RNA molecules.

The purified first-strand cDNA molecules were then divided into 2 equal aliquots and dried. To the first aliquot, 1.5 nmol (7.5 µL) of the oligonucleotide sequence tag (Seq. ID. No. 2; GACGAAGACAGTAGACAN$_x$(N(2'-O-Methyl))(3'-C3 propyl spacer) note that x is 6) was added and to the second aliquot, 7.5 µL water. Both aliquots were incubated at 65° C. for 5 min and then at 37° C. for 10 min. Thereafter, each aliquot was adjusted to 20 µL by adding components of a DNA synthesis reaction, at final concentrations of 1 mM Tris-HCl (pH 7.5), 0.5 mM $MgCl_2$, 0.75 mM DTT, 33 µM dATP, 33 µM dGTP, 33 µM dCTP, 33 µM TTP and 0.5 units/µL Klenow fragment (3' to 5' exo$^-$) (New England Biolabs). The reactions were incubated for an additional 60 minutes at 37° C. and then terminated with the addition of phenol. The first DNA templates formed in reaction 1 (see schematic of FIG. 2 for illustration) was then purified from any excess sequence tag oligonucleotide by size selection (Amersham) in a final volume of approximately 40 uL. The first-strand cDNA molecule from reaction 2 was similarly purified although it did not contain any oligonucleotide sequence tag.

The random sequence at each nucleotide position was synthesized from an equal mixture of the four phosphoramidites by TrLink Biotechnologies (San Diego, Calif.) and the oligonucleotide was PAGE purified. The length of the random portion in each example is seven.

EXAMPLE 2

Transcription of the First DNA Templates

Figure 4:
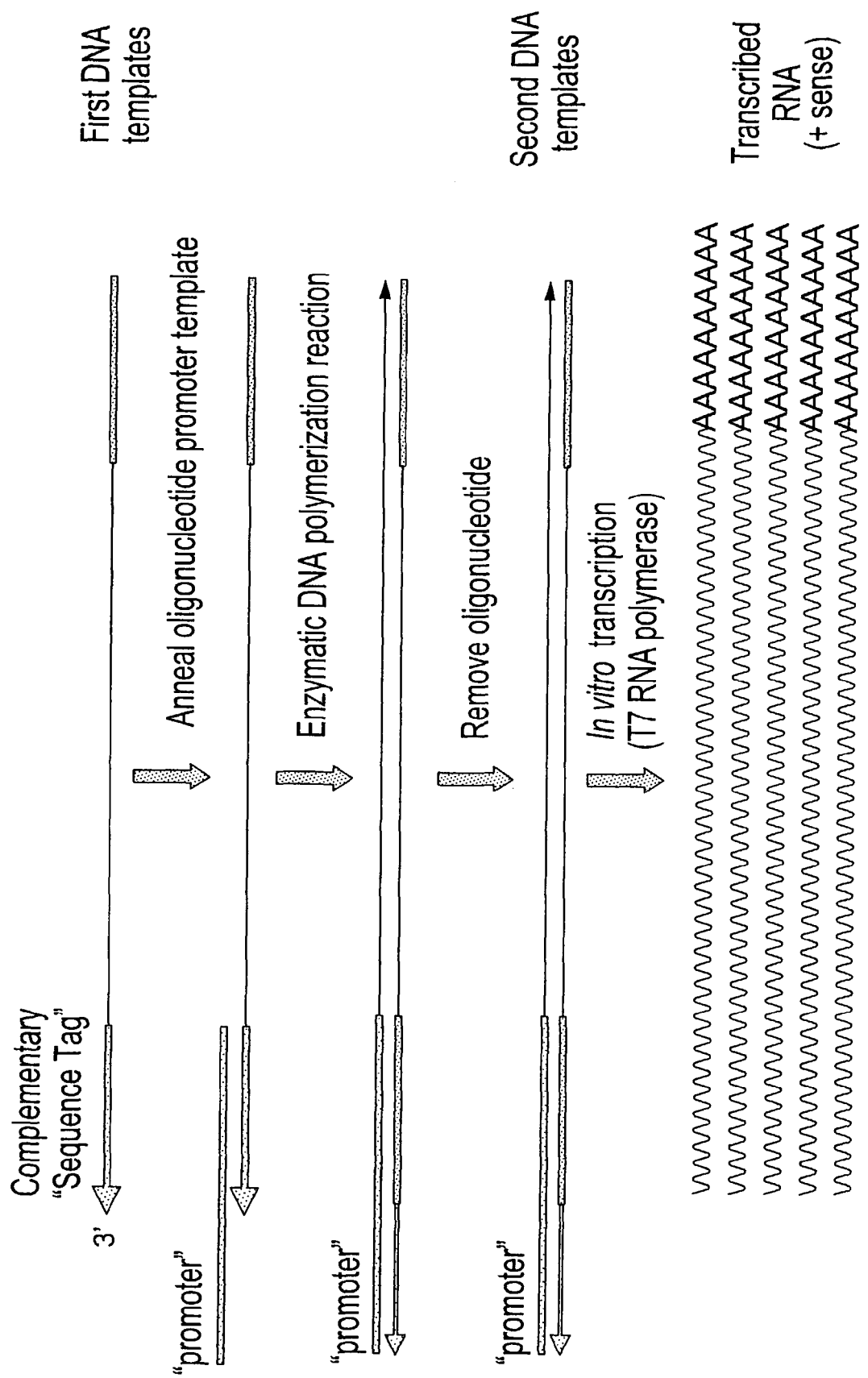
FIG. 4 shows a schematic illustration of the synthesis of second DNA templates containing a promoter sequence and transcription of RNA from second DNA template.

The DNA templates from each of the 2 reactions in Example 1 were used for priming DNA synthesis using a second oligonucleotide template containing a 5' T7 promoter sequence (italicized) and a 3' sequence tag (Seq. ID. No. 3; AATTCTAATACGACTCACTATAGG-GAGACGAAGACAGTAGACA) similar to the sequence tag contained in the first oligonucleotide to form second DNA templates containing a T7 promoter sequence. The DNA synthesis reactions (50 uL) contained the respective DNA templates, 5 pmoles second oligonucleotide template (Seq. ID. No. 3), 40 mM Tricine-KOH (pH 8.7), 15 mM KOAc, 3.5 mM $Mg(OAc)_2$, 3.75 µg/mL BSA, 0.005% Tween-20, 0.005% Nonidet-P40, 200 µM dATP, 200 µM dGTP, 200 µM dCTP, 200 µM TTP and 2 µL Advantage 2 Polymerase mix (BD Biosciences). The reactions were heated at 95° C. for 1 minute 30 seconds, 50° C. for 1 minute, 55° C. for 1 minute and finally, 68° C. for 30 minutes before phenol was added to terminate the reaction. In addition to DNA synthesis primed from the first DNA templates using the second oligonucleotide template as template, DNA synthesis could as well be primed from the second oligonucleotide template using the first DNA templates as template in the same reaction (see schematic of FIG. 4 for illustration) to form completely double-stranded second DNA templates. The resulting DNA templates from both reactions were purified by size selection (Amersham) and transcribed in vitro.

Figure 5A:
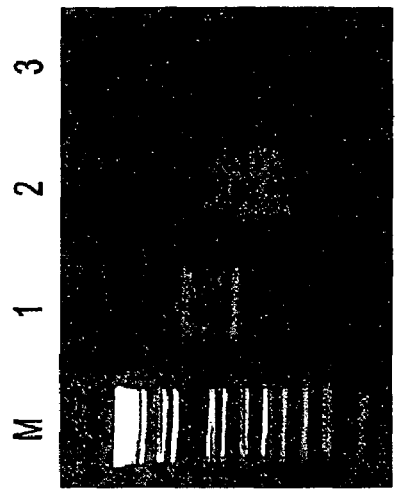
FIG. 5 shows agarose gel electrophoretic analysis of the products of transcription reactions from second DNA template with or without a terminal sequence tag, as detected by ethidium bromide staining (A) or by blot hybridization with $^{32}$P labeled cDNA probes to GAPDH (B) and β-actin (C)
Figure 5C:
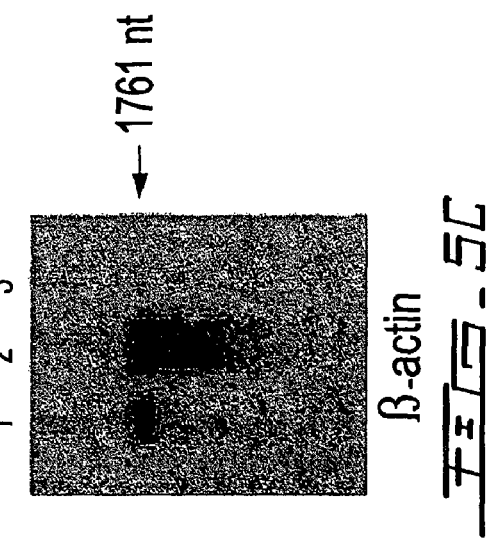
Figure 5B:
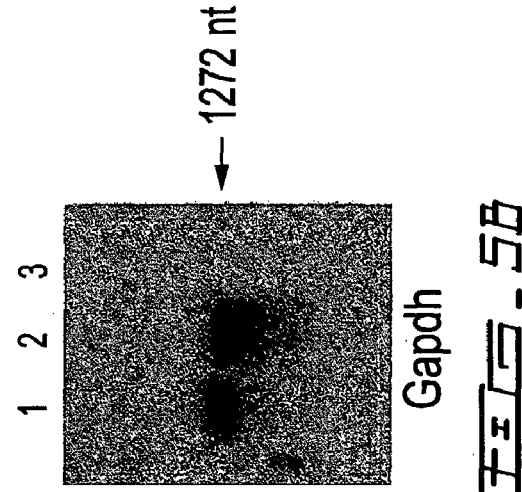

Each in vitro transcription reaction (40 µL) comprised the respective DNA templates, 40 mM Tris-HCl (pH 7.9), 6 mM $MgCl_2$, 2 mM spermidine, 10 mM DTT, 0.5 mM ATP, 0.5 mM GTP, 0.5 mM CTP, 0.5 mM UTP and 4 µL T7 RNA polymerase (Ambion). The reactions were incubated at 37° C. for at least 2 hours, digested with DNase I at 37° C. for 30 minutes, phenol extracted and purified. An equal quantity from each transcription reaction was analyzed by agarose gel electrophoresis and Northern blot hybridization with $^{32}P$ labeled cDNA probes for GAPDH and β-actin (BD Biosciences). As shown in FIG. 5, at A, Lane 1 contains 200 ng of neat total RNA from mouse brain, Lane 2 contains a 4-μL aliquot of the transcription reaction from the second DNA templates containing the T7 promoter sequence and Lane 3 contains a 4-μL aliquot of the transcription reaction from DNA templates prepared without the addition of the oligonucleotide sequence tag (cDNA molecules) (Seq. ID. No. 2). In Lane 2, RNA of various sizes (a RNA smear ranging from ~300 bp to ~1650 bp based on the 1 Kb Plus DNA ladder (InVitrogen)), as expected from a library of cDNA molecules, were synthesized from the second DNA templates whereas, in Lane 3, no such RNA was observed. The Northern blot analysis (FIG. 5 at B and C, Lane 2) confirms the presence of both GAPDH and β-actin sequences in the amplified RNA, and the majority of the transcribed RNA species corresponding to these two genes migrated at approximately the expected full-length molecular weight positions in comparison to the respective full-length bands (GAPDH (1272 bp; mRNA Accession # X01677) and β-actin (1761 bp; mRNA Accession # X00351) seen for the neat total RNA (FIG. 5 at B and C, Lane 1). Also, there was no hybridization signal seen for either gene when no transcribed RNA synthesized was present (FIG. 5 at B and C, Lanes 3). These results suggest that the preferred reaction for the attachment of the second oligonucleotide template containing the promoter sequence (Seq. ID. No. 2) was primarily at the 3'-ends of the first DNA templates.

FIG. 5 contains the following:
Lane 1—200 ng total RNA from mouse brain
Lane 2—4 μL transcribed RNA from second DNA templates
Lane 3—4 μL transcribed RNA from cDNA molecules

EXAMPLE 3

Amplification in PCR of Specific DNA Sequences Contained in a Library of First DNA Templates Using a First Primer Corresponding to the Oligonucleotide Sequence Tag and Gene Specific Second Primers In vitro transcribed RNA (5 μg) generated in Example 2 containing the oligonucleotide sequence tag at its 5' proximal end was reverse transcribed in a standard cDNA synthesis reaction (InVitrogen) and the resulting first-strand cDNA was purified and reconstituted in 20 μL H$_2$O. Four PCR amplification reactions were assembled, each containing 40 mM Tricine-KOH (pH 8.7), 15 mM KOAc, 3.5 mM Mg(OAc)$_2$, 3.75 μg/mL BSA, 0.005% Tween-20, 0.005% Nonidet-P40, 200 μM dATP, 200 μM dGTP, 200 μM dCTP, 200 μM TTP and 2 μL Advantage 2 Polymerase mix in a final volume of 50 μL. To reactions 1 and 2, 20 picomoles of each of a forward primer (first primer) (Seq. ID. No. 4; TTGGCGCGCCTTGG-GAGACGAAGACAGTAGA), which is complementary to the sequence tag on the 3' proximal end of the synthesized cDNA and a gene specific reverse primer (second primer) for GAPDH (Seq. ID. No. 5; CATGTGGGCCATGAGGTC-CACCAC) were added. Similarly, to reactions 3 and 4, 20 picomoles of each of the same first primer (Seq. ID. No. 4) and instead, a specific reverse primer (second primer) for β- or γ-actin (Seq. ID. No. 6; CGTCATACTCCTGCTTGCT-GATCCACATCTGC) were added. Additionally, to reactions 2 and 4, 2-μL aliquots of the reverse transcribed first-strand cDNA templates were added, whereas, to reactions 1 and 3, 2-μL aliquots of water were added instead. All four reactions were amplified using PCR for 25 cycles—each cycle comprising 95° C. for 1.5 minutes, 55° C. for 2 minutes and 68° C. for 3 minutes followed by a final extension at 68° C. for 30 minutes. A 5-μL aliquot from each reaction was analyzed by agarose gel electrophoresis and Southern blot hybridization with $^{32}$P labeled cDNA probes for GAPDH and β-actin (BD Biosciences).

Figure 6A:
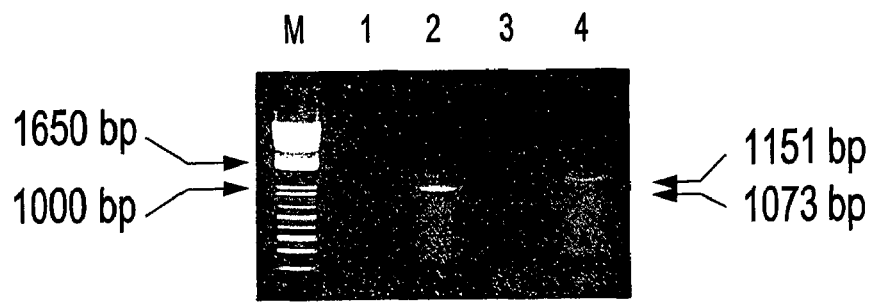
FIG. 6 shows agarose gel electrophoretic analysis of products from PCR amplification of tagged (or untagged) second DNA template prepared with or without a terminal sequence tag and a common forward primer (first primer) in combination with gene specific reverse primers (second primers) for GAPDH and actin, as detected by ethidium bromide staining (A) or by blot hybridization with $^{32}$P labeled cDNA probes to GAPDH (B) and β-actin (C)
Figure 6B:
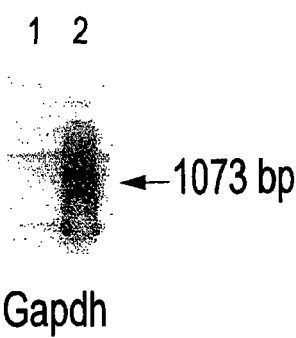
Figure 6C:
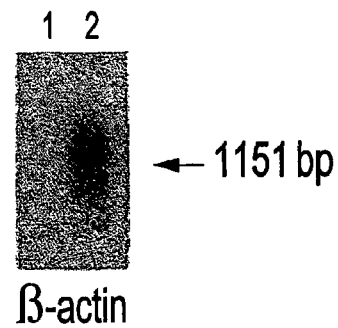

As shown in FIG. 6 at A, Lanes 1 and 3, which contained no tagged cDNA, gave no amplified products and only the primers were visible. On the other hand, Lanes 2 and 4 contained amplified products and in each case, a major product band was observed migrating at the expected molecular weight for the GAPDH (1073 bp) or β-actin (1151 bp) products respectively, which corresponded to the sequence tag present at the proximal 3' ends of the respective full-length cDNA species. Southern blot analysis (FIG. 6 at B and C, Lanes 2 and 4) confirms the amplified products as GAPDH and β-actin respectively. It is also possible that the β-actin probe will hybridize to γ-actin sequences, which will be amplified by these primers as well.

FIG. 6 contains the following:
Lane 1—no added template
Lane 2—2 μL aliquot of oligo-tagged first-strand cDNA as template

EXAMPLE 4

Verification of the Presence of the Oligonucleotide Sequence Tag at the 3'-Ends of First DNA Templates A 2-μL aliquot of the PCR-amplified materials for β-/γ-actin as generated in Example 3, reaction #4, was used as template in a secondary PCR reaction containing the first primer (Seq. ID. No. 4) and a gene specific reverse primer for β-/γ-actin (Seq. ID. No. 7; AACCCTGCGGCCGCCA-CATCTGCTGGAAGGTGGACA) now containing a 5' Not I restriction endonuclease site to aid in cloning. The PCR reaction was performed as described in Example 3. The completed PCR reaction was then purified using the Qia-PCR clean-up procedure (Qiagen) and products corresponding to 50% of the purified reaction was concentrated and separated by agarose gel electrophoresis. A major product band corresponding to actin was then excised and digested with restriction endonucleases Asc I and Not I, in a 50-μL reaction comprising 20 mM Tris-acetate 9 (pH 7.9), 50 mM KOAc, 1 mM DTT, 100 μg/mL BSA and 10 units of each enzyme (NEB). The digestion reaction was incubated at 37° C. for 3 hours, purified using the Qia-PCR clean-up procedure, concentrated into a 2-μL aliquot and used in a ligation reaction. The ligation reaction comprised Asc I-Not I digested PCR amplicons (2 μL) and 20 ng plasmid vector (pCATRMAN) for cloning in E. coli, 50 mM Tris-HCl (pH 7.5), 10 mM MgCl$_2$, 10 mM DTT, 1 mM ATP, 25 μg/mL BSA and 400 units T4 DNA ligase (NEB). The ligation reaction was incubated at 16° C. overnight, which was followed by 65° C. for 10 minutes. To the ligation reaction, 90 μL H$_2$O and 1 mL butanol were added, mixed, and the precipitate collected by centrifugation and reconstituted in 4 μL H$_2$O. A 2-μL aliquot was then used to transform E. coli (DH10B) by electroporation (Invitrogen). After incubating the electroporated cells at 37° C. in 1 mL SOC complete media (Sambrook et al., 1990) for 1 hour, 1 μL and 10 μL aliquots were plated on YT agar plates containing 100 μg/mL ampicillin and grown at 37° C. overnight. Next, 30 colonies were picked directly into 50 μL aliquots of H$_2$O and 43 μL of each aliquot added to individual PCR reactions comprising 10 μL 10× reaction buffer (Qiagen), 0.2 mM dATP, 0.2 mM dGTP, 0.2 mM dCTP, 0.2 mM TTP, 20 pmoles forward primer (Seq. ID. No. 8; AAT-CACTGGACGCGTGGC), 20 pmoles reverse primer (Seq. ID. No. 9; GGAAACAGCTATGACCATG) and 3 units Hot start Taq DNA polymerase (Qiagen). The reactions were heated at 99° C. for 10 minutes followed by 30 cycles of 95° C. for 1.5 minutes, 55° C. for 1 minute, 72° C. for 2 minutes and a final extension at 72° C. for 15 minutes. A 5-μL aliquot of each reaction was then analyzed by agarose gel electrophoresis for the presence of PCR amplicons before proceeding to sequence analysis.

For sequence analysis, a 5-μL aliquot from 24 amplification reactions containing a PCR amplicon was used in the Big Dye Automated DNA sequencing procedure (Applied Biosystems Inc.) using Seq. ID. No. 8, as the sequencing primer. Table 1 below shows the first 80 nucleotides of 5' terminus of the DNA sequences obtained for the γ-actin clones sequenced. It appears that each of the 24 clones contained a sequence corresponding to γ-actin rather than β-actin. More important though, in each case, the oligonucleotide sequence tag (Seq. ID. No. 2) was present at the 3' proximal end of all cDNA fragments cloned for γ-actin (shown as bold and italicized fonts) whether or not, the cDNA fragment was synthesized to the extreme 5'-terminus of the mRNA species or terminated prematurely at various positions during the cDNA synthesis reaction. The additional 4 nucleotides (GGGA) upstream of the tag sequence represent the transcription initiation site of the T7 promoter. In general, the majority of the clones contain the tag sequence affixed at the 5' terminus of the known full-length sequences γ-actin (from 4 bases upstream (−4) of Accession # BC023248.1 to 8 bases (+8) downstream of Accession # AK076081.1) (Table 1). However, there were some clones for γ-actin (Table 1, clones #22, #23 and #24) that were tagged at different positions more internally, which likely represented different termination positions during cDNA synthesis. These results clearly indicate that regardless of the terminal sequence at the 3'-ends of cDNA fragments, an appropriate oligonucleotide sequence tag will likely become appended following the teachings as described in Example 1.

Table 1 shows a summary of approximately the first 80 nucleotides from the 5' ends of the γ-actin clones that were sequenced to demonstrate the presence of the oligonucleotide sequence tag (shown italicized and bolded).

EXAMPLE 5

Linear Transcription of Libraries of Second DNA Templates as Demonstrated by the Detection of a Specific Gene Sequence (Cathepsin K)

Total RNA from undifferentiated (precursor) and fully differentiated (osteoclast) mouse RAW 264.7 cells was extracted using a Trizol method (InVitrogen), purified further by RNeasy (Qiagen) and quantified at $A_{260\ nm}$. The precursor and osteoclast specific total RNA samples were then mixed in the following ratios:

1. 500 ng precursor+0 ng osteoclast total RNA
2. 400 ng precursor+100 ng osteoclast total RNA
3. 250 ng precursor+250 ng osteoclast total RNA
4. 100 ng precursor+400 ng osteoclast total RNA
5. 0 ng precursor+500 ng osteoclast total RNA First-strand cDNA was then synthesized from each RNA or RNA mixture and first DNA templates prepared using the oligonucleotide sequence tag (Seq. ID. No. 2) according to the teachings of Example 1. Each first DNA templates was subsequently annealed to a second oligonucleotide template containing a T7 promoter sequence and a oligonucleotide sequence tag complement to tag sequence contained in the first DNA templates (Seq. ID. No. 3) and an enzymatic DNA polymerization reaction for each performed as described in Example 2. The resulting second DNA templates containing a double-stranded T7 promoter for each reaction was purified and transcribed in vitro using T7 RNA polymerase as described in Example 2. An equal amount of RNA (500 ng) from each transcription reaction was analyzed by agarose gel electrophoresis and Northern blot hybridization to a $^{32}P$ labeled cDNA probe specific for mouse cathepsin K gene.

Figure 7A:
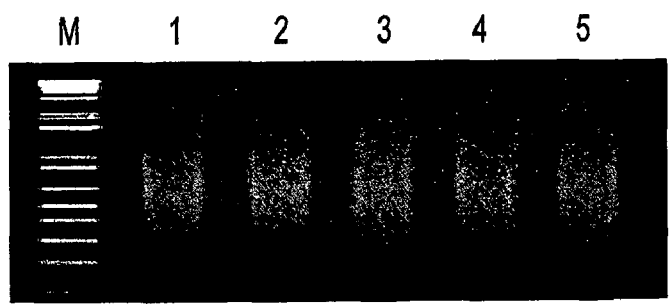
FIG. 7 shows agarose gel electrophoretic analysis of the products of transcription reactions from cDNA prepared with a terminal sequence tag, as detected by ethidium bromide staining (A) or by blot hybridization with $^{32}$P labeled cDNA probes to Cathepsin K (B)
Figure 7B:
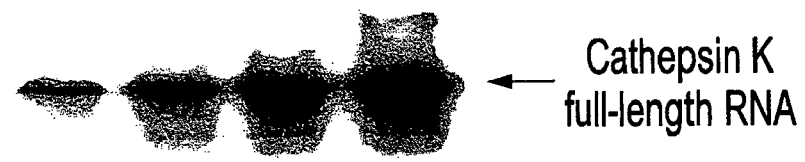

FIG. 7 at A, Lanes 1-5 show the library of linearly transcribed RNA synthesized from the second DNA templates corresponding to the various RNA and RNA mixtures and in all cases, the profile of the transcribed RNA appear to be similar. FIG. 7 at B, Lanes 1-5 show the Northern blot hybridization results for the cathepsin K gene—Lane 1, representing the 100% precursor RNA, showed no cathepsin K signal since this is an osteoclast-specific gene and is not expected to be seen in the precursor sample.

Linearity of amplification was thus achieved using the methods described herein.

TABLE 1

| SPECIFIC SEQUENCE | CLONE # | Sequences (5'-80 nt) | 5' Terminus relative to Accession # BC023248.1/ AK076081.1 |
|---|---|---|---|
| γ-actin | 1-18 (SEQ ID NO. 10) | GGGAG *ACGAAGACAGTAGACA*CTCCGCCGCCGGCT TACACTGCGCTTCTTGCCGCTCCTCCGTCGCCGCCG CGTCCTTCG | −2/+8 |
| | 19-21 (SEQ ID NO.11) | GGGA *GACGAAGA CAGTAGACA*CACTCCGCCGCCG GCTTACACTGCGCTTCTTGCCGCTCCTCCGTCGCCG CCGCGTCCTTCG | −4/+6 |
| | 22 (SEQ ID NO. 12) | GGGA *GACGAAGA CAGTAGACA*CGGGGTCACACACA CAGTGCCCATCTATGAGGGCTACGCCCTTCCCCACG CCATCTTGC | +537/+546 |
| | 23 (SEQ ID NO. 13) | GGG *AGACGAAG ACAGTAGACA*TTCAGGCGGTGCTG TCCTTGTATGCATCTGGGCGCACCACTGGCATTGTC ATGGACTCT | +473/+482 |
| | 24 (SEQ ID NO. 14) | GGGA *GACGAAGACAGTAGACA*AGCTAACAGAGAGA AGATGACGCAGATAATGTTTGAAACCTTCAATACCCC AGCCATGT | +405/+414 |

However, Lanes 2-5 show increasing levels of the cathepsin K gene corresponding to the increasing starting amounts of osteoclast RNA (25%-100%) in each RNA mixture. In order to quantify the cathepsin K signal, each of the five lanes of the Northern blot was excised and the radioactivity measured by scintillation counting. The counts per minute (cpm) obtained for each of the five lanes, minus the background, was then plotted against the corresponding total RNA or RNA mixtures. As shown in FIG. 8, a linear relationship between the increasing levels of osteoclast total RNA in the RNA mixture and the level of cathepsin K signal was observed. This indicates that the tagging procedure does not appear to introduce a bias for this targeted sequence within the total RNA input range tested.

FIG. 7 contains the following:
Lane 1—500 ng transcribed RNA from 100% precursor
Lane 2—500 ng transcribed RNA from 75% precursor+ 25% osteoclast
Lane 3—500 ng transcribed RNA from 50% precursor+ 50% osteoclast
Lane 4—500 ng transcribed RNA from 25% precursor+ 75% osteoclast
Lane 5—500 ng transcribed RNA from 100% osteoclast

EXAMPLE 6

Sensitivity of the Selective Terminal Tagging Procedure

Total RNA was extracted from aliquots of 1000, 5000, 10000, 50000, 100000 and 1000000 undifferentiated mouse RAW 264.7 cells by a Trizol method (InVitrogen) and purified further by RNeasy (Qiagen). The 1 million RAW264.7 cells sample yielded 27.4 µg of total RNA, of which approximately 1% (270 ng) was mRNA. The amounts of total RNA purified from the 1000-100000 samples were not quantified. Rather, the whole amount of total RNA extracted from each cell dilution was used directly in the tagging and transcription procedures. In addition, dilutions of total RNA isolated from the 1 million cells sample representative of 1000, 5000, 10000, 50000 and 100000 cells were similarly tagged and transcribed, in order to determine the efficiency of the method.

The mRNA population in each RNA sample was used for making first-strand cDNA and each cDNA was tagged with the oligonucleotide sequence tag (Seq. ID. No. 2) to generate first DNA templates and purified according to Example 1. Each first DNA templates was subsequently annealed to the second oligonucleotide containing a sequence tag complement to the tag contained in the first DNA templates and a T7 promoter sequence (Seq. ID. No. 3), and an enzymatic DNA polymerization reaction for each performed as described in Example 2. The resulting second DNA templates containing the double-stranded T7 promoter for each reaction was purified and transcribed in vitro using T7 RNA polymerase as described in Example 2. In order to perform a second round of transcription, the transcribed RNA produced from the first transcription reaction for each sample was used to synthesize first-strand cDNA according to Example 1. Each cDNA mixture was then used with the second oligonucleotide template (Seq. ID. No. 3) for second-strand DNA synthesis. Then, each resulting double-stranded T7 promoter containing DNA templates was transcribed using T7 RNA polymerase, according to Example 2. The quantity of RNA obtained for each total RNA sample after two rounds of transcription is summarized in Table 2. Table 2 shows the sensitivity of the terminal tagging procedure comparing purified total RNA diluted from a concentrated stock or purified directly from dilutions of cells.

TABLE 2

| Cell Number | Total RNA (ng)* | Amplified RNA (µg) | |
|---|---|---|---|
| | | RNA Dilution | Cell Dilution |
| 100000 | 2700 | 73 | 30 |
| 50000 | 1400 | 41 | 9.6 |
| 10000 | 270 | 9.6 | 2.4 |
| 5000 | 140 | 5.9 | 2.2 |
| 1000 | 27 | 1.2 | — |

*based on recovery of 27 µg total RNA from $10^6$ cells

Although the quantity of amplified RNA was linear with respect to the amount of input RNA, the relative amplification efficiency increases throughout the range. An aliquot of 27 ng of total RNA, representing 270 pg of mRNA and 1000 cells, produced 1.2 µg of amplified RNA, an amplification efficiency of 4400 fold. However, no amplified RNA was detected using RNA that was extracted directly from 1000 cells. This is likely due to non-quantitative recovery of RNA from the small sample. With the existing methods of RNA extraction, 5000 cells are involved for the direct amplification of RNA. In an average of 2 experiments, 2.2 µg RNA were amplified from the total RNA that was extracted directly from 5000 cells. By improving the recovery of RNA from small samples, we may expect at least 1 µg of amplified RNA from 1000-2000 cells.

EXAMPLE 7

Attachment of a Modified Oligonucleotide Sequence Tag to the Terminal 3' ends of cDNA Molecules and Synthesis of Completely Double-Stranded "Second DNA Templates Followed by In Vitro Transcription"

The modified selective terminal tagging method was initially compared to the standard method described in the above mentioned EXAMPLES using an input of 100 ng total RNA from fully differentiated mouse RAW 264.7 osteoclasts. The results showed no difference in the yield and quality of the transcribed RNA from both methods (data not shown). Thus, this ensuing example describes the use of a 2 ng input total RNA, in order to further test the sensitivity the modified method compared to the standard method, which is already known to perform well at this level. First-strand cDNA was synthesized from two 2 ng samples of total RNA purified from fully differentiated mouse RAW 264.7 osteoclasts according to the teachings of Example 1 with the exception that RNase I was used instead of RNase A. Upon completion of the cDNA synthesis and RNA hydrolysis, one 2 ng reaction was subjected to the standard process for synthesis of first DNA templates and completely double-stranded second DNA templates as described in Example 1 and Example 2.

To the second 2 ng cDNA reaction at 37° C., 1500 pmoles of the modified primer (Seq. ID. No 15: AATTCTAATAC-GACTCACTATAGGGAGACGAAGACAGTA-GACArNrNrNrNrNrNrN(N(2'-O-Methyl))(3'-C3 propyl spacer) was added and allowed to incubate for 10 minutes before a 12-µL aliquot of a mixture comprising 1.67×cDNA reaction buffer (In Vitrogen), 17 mM DTT, 1.67 mM dATP, 1.67 mM dGTP, 1.67 mM dCTP, 1.67 mM TTP, 0.33 U/µL RNase H (In Vitrogen) and 2.5 U/µL AMV reverse transcriptase (In Vitrogen) was added to the reaction tube. The reaction was then incubated at 50° C. for 30 minutes. In this reaction, RNase H digestion resulted in the removal of at least the 3' terminus blocking nucleotide from the promoter oligonucleotides sequence tag template and thus, converted the promoter sequence tag oligonucleotides template to oligonucleotides primer for directing DNA synthesis using AMV reverse transcriptase.

Figure 9A:
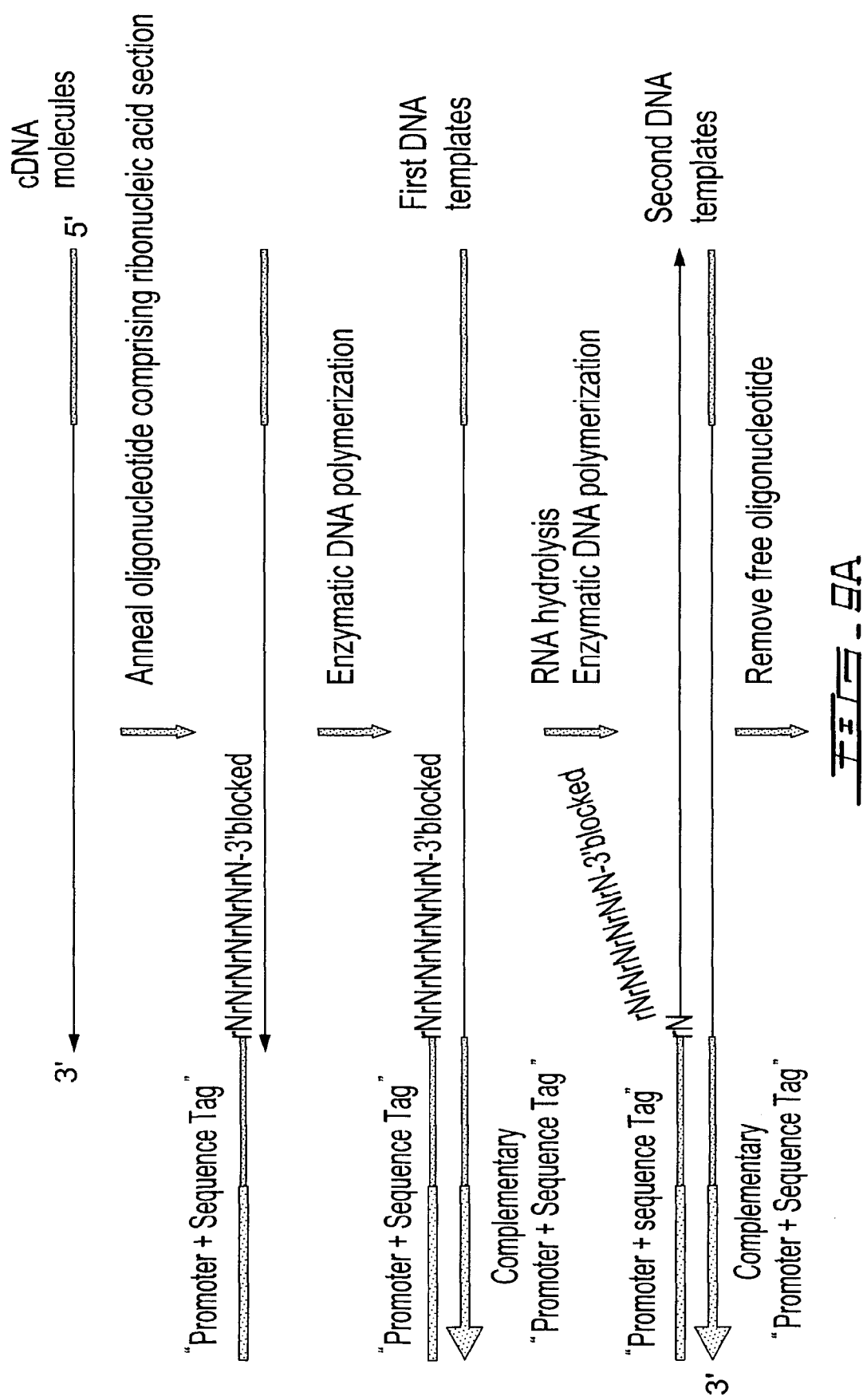
FIG. 9a is a schematic illustrating the terminal tagging of a cDNA molecule using an improved method according to an embodiment of the present invention.
Figure 10A:
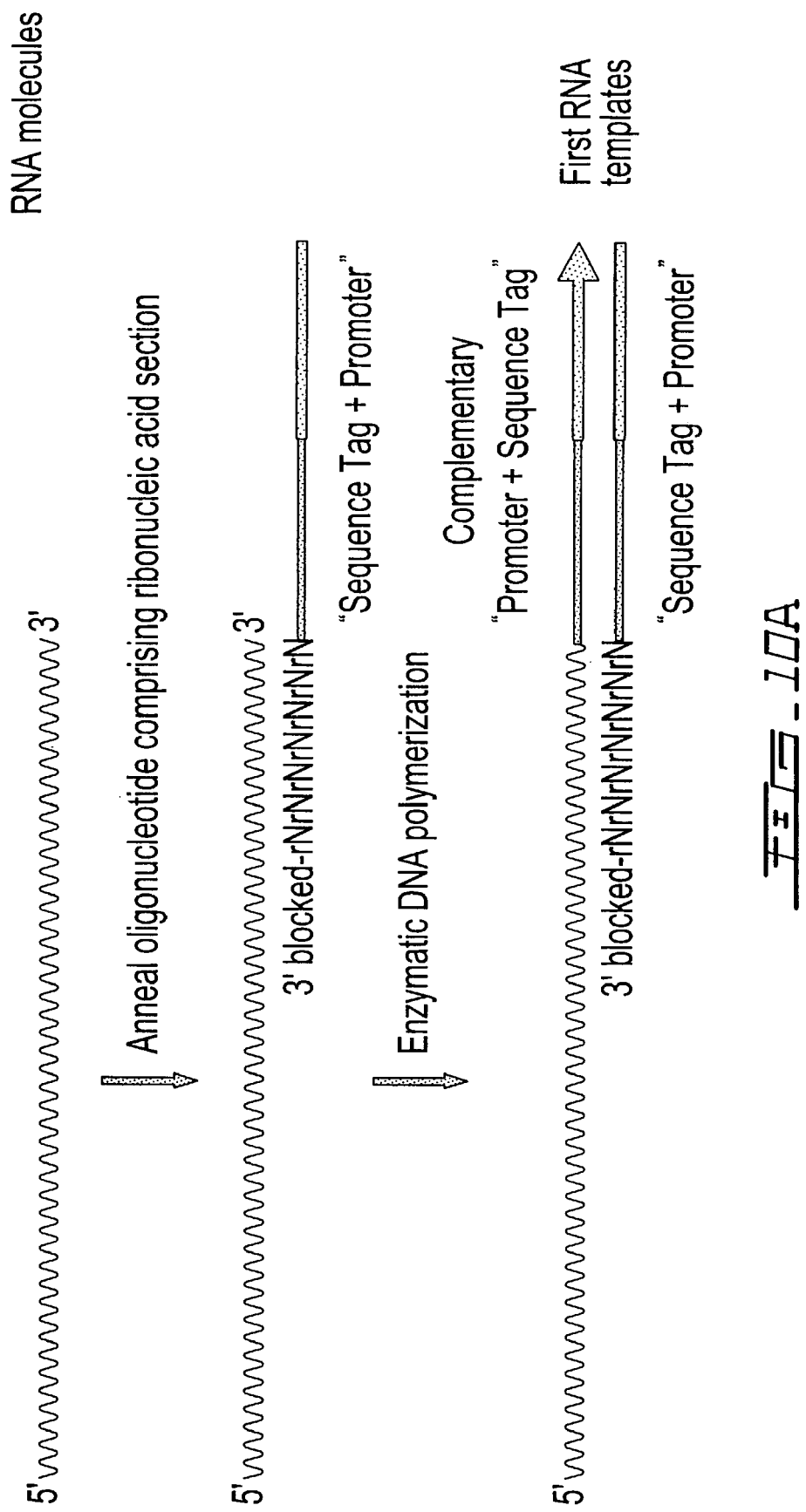
FIG. 10*a* is a schematic illustrating the terminal tagging of a RNA molecule using an improved method according to an additional embodiment of the present invention.
Figure 10B:
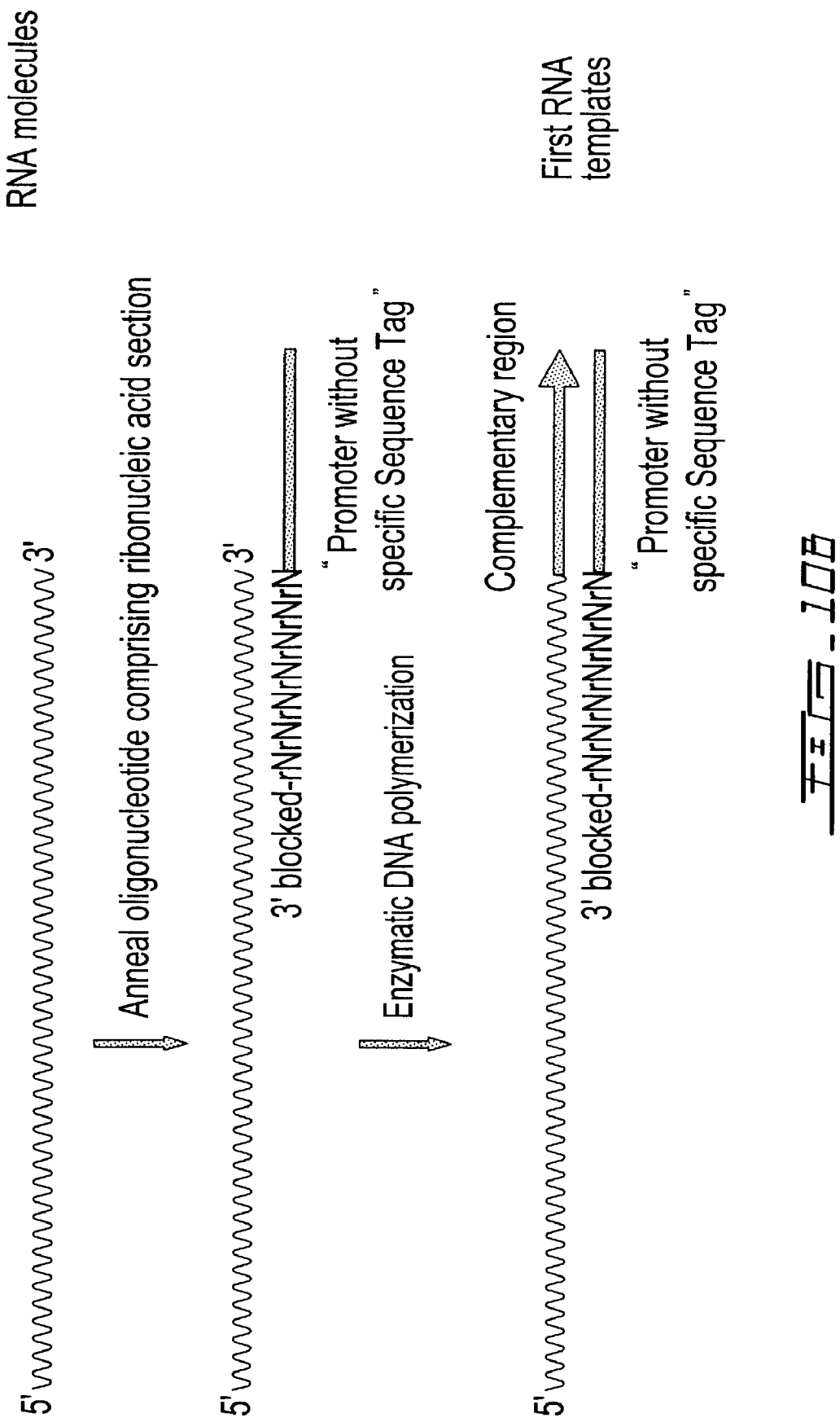
FIG. 10*b* is a schematic illustrating the terminal tagging of a RNA molecule using an improved method according to a further embodiment of the present invention.
Figure 11:
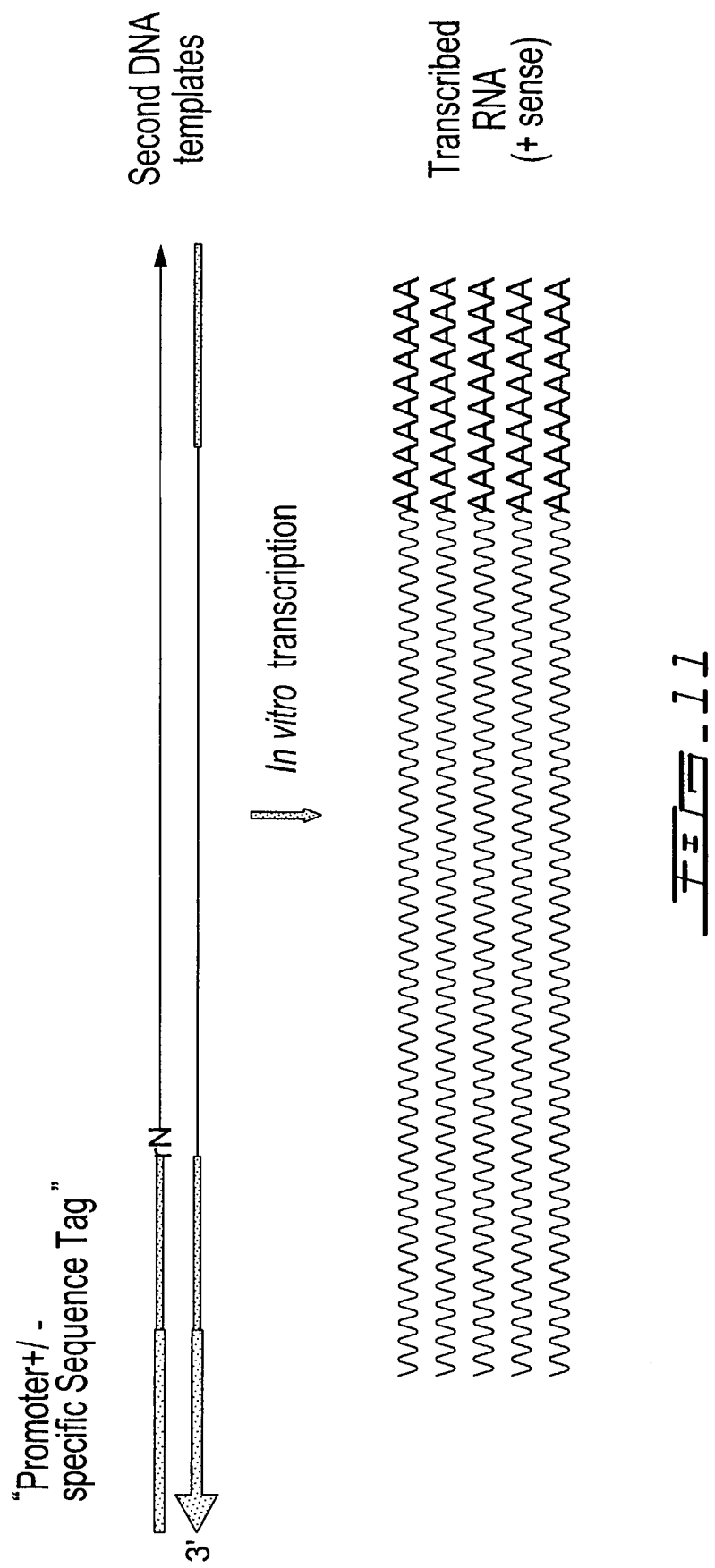
FIG. 11 is a schematic illustrating linear RNA amplification from the second DNA template according to yet an additional embodiment of the invention.

Following synthesis of the double-stranded second DNA templates (FIG. 9a), the nucleic acids in the reaction mixture was purified using Qiagen MinElute Kit. However, it is contemplated that this purification step of the second DNA templates prior to transcription may not be required. The purified tagged second DNA templates from both the 2 ng-standard and 2 ng-modified samples were added to separate 40-μL in vitro transcription reaction (Ambion) according to the teachings of Example 2 and each transcription reaction was allowed to proceed at 37° C. for 4 hours. The RNA synthesized from each reaction was subjected to a second round of transcription amplification following the teachings of Example 6. The transcribed RNA after the second round was purified (Qiagen Rneasy Kit) and quantified at $A_{260nm}$. A similar quantity of transcribed RNA was obtained for each sample showing comparable sensitivity. A 200 ng of each transcribed RNA (standard and modified methods) was analyzed by agarose gel electrophoresis and Northern blot hybridization to $^{32}P$ labeled cDNA probes specific for GAPDH and mouse TRAP genes. Also, 200 ng of the total RNA was compared on the same agarose gel.

FIG. 12—panel A, Lanes 2 and 3 show the electrophoretic profile of the transcribed RNA RNA for the standard method and the modified method respectively. In both cases, the profile of the transcribed RNA appears to be similar. FIG. 12—panel B, Lanes 2 and 3 show the Northern blot hybridization results for the GAPDH and TRAP genes. Comparing the hybridization pattern in Lane 2 (standard method) and Lane 3 (modified method) with that of total RNA (Lane 1), it is evident that the full-length RNA present for both genes was essentially similar for both methods used. These results suggest that the modified method, which is more simplified and homogeneous, and uses 2 instead of 3 oligonucleotides for terminal tagging and efficient RNA synthesis, is a significant improvement to the standard method.

FIG. 12 contains the following:
M—molecular weight marker
Lane 1—200 ng osteoclast total RNA
Lane 2—200 ng transcribed RNA from 2 ng osteoclast total RNA (standard method)
Lane 3—200 ng transcribed RNA from 2 ng osteoclast total RNA (modified method)

EXAMPLE 8

Selective Terminal Tagging of cDNA with a Promoter Containing Sequence Tag Oligonucleotides Comprising Deoxynucleotides and a Blocked 3' Terminus Followed by RNA Synthesis from the Single-Stranded cDNA Template Strand First-strand cDNA was synthesized from two 50 ng samples of total RNA purified from fully differentiated human osteoclasts according to the teachings of Example 1. Following RNA hydrolysis, one 50 ng cDNA reaction was tagged with Seq. ID. No. 2 following the teachings as described in Examples 1 with the exception that AMV reverse transcriptase in the supplier's reaction buffer (In Vitrogen) was used instead of Klenow's fragment (3' to 5' exo⁻). Transcription of the resulting first DNA templates was then performed according to the teachings of Example 2 in order to synthesize amplified RNA.

To the second 50 ng cDNA reaction, tagging was performed using 1500 pmoles of the promoter containing sequence tag oligonucleotides comprising deoxynucleotides and a blocked 3' terminus (Seq. ID. NO. 16: AAT-TCTAATACGACTCACTATAGGGAGAC-GAAGACAGTAGACANNNNNN(N(2'-O-Methyl))(3'-C3 propyl spacer) was added instead of Seq. ID. NO. 2 and the tagging reaction according to the teachings of Example 1 was performed with the exception that AMV reverse transcriptase in the supplier's reaction buffer was used instead of Klenow fragment (3' to 5' exo⁻). Following this tagging reaction, the first DNA templates are formed comprising a functional double-stranded promoter sequence and a single-stranded cDNA template strand since DNA polymerization from the 3' terminus of the sequence tag oligonucleotides template was blocked. The first DNA templates comprising the double-stranded promoter was purified using Qiagen MinElute Kit and RNA synthesized directly in an in vitro transcription reaction as described in Example 2 above.

The RNA synthesized from each 50 ng cDNA tagging reactions was then subjected to a second round of transcription amplification following the teachings of Example 6. The transcribed RNA after the second round for each reaction was purified (Qiagen Rneasy Kit) and quantified at $A_{260nm}$. Table 3 below shows the respective RNA yields from the fully double-stranded second DNA templates formed using SEQ. ID. NO. 2 and single-stranded first DNA templates comprising the double-stranded promoter formed using SEQ. ID. NO. 16. Although the procedure using SEQ. ID. NO 16 produced a similar quality transcribed RNA as SEQ. ID. NO. 2 as determined by electrophoresis and hybridization analysis, the yield was approximately 80% lower.

TABLE 3

Transcribed RNA Yields from the double-stranded second DNA templates formed using SEQ. ID. NO. 2 and single-stranded first DNA templates comprising a double-stranded promoter formed using SEQ. ID. NO. 16.

| Input Total | Transcribed RNA Yields (μg) | |
| --- | --- | --- |
| RNA (ng) | SEQ. ID. NO. 2 Procedure | SEQ. ID. NO. 16 Procedure |
| 50 | 91 | 17 |

EXAMPLE 9

Comparison of Different Oligonucleotide Sequence Tags

First-strand cDNA was synthesized from six 50 ng samples of total RNA purified from fully differentiated human osteoclasts according to the teachings of Example 1. After RNA hydrolysis, the following tagging reactions were performed as described in Examples 1 with the exception that AMV reverse transcriptase in the supplier's reaction buffer (In Vitrogen) was used instead of Klenow's fragment (3' to 5' exo⁻): (1) two 50 ng cDNA reaction were tagged with two different synthesis of the oligonucleotide sequence tag corresponding to Seq. ID. No. 2, (2) three 50 ng cDNA reactions were tagged with a different oligonucleotide sequence tag corresponding to SEQ ID NO.: 17 (GCCTGCACCAACAGTTAACA-GANNNNNN(N-2'-O-Methyl)-3'-C3 propyl spacer) and (3)

one 50 ng cDNA reaction was tagged with a different oligonucleotide sequence tag corresponding to SEQ ID NO.:18 (GCCTGCACCAACAGTTCACAGANNNNNN (N-2'Omethyl)-3'-C3 propyl spacer). For the three different oligonucleotide sequence tags, the randomized portion of each sequence and the 3' terminus blocking group remained the same. The DNA templates from each of the tagged reactions were used for priming DNA synthesis using a second oligonucleotide template containing a 5' T7 promoter sequence (italicized) and a 3' sequence tag complement corresponding to the respective sequence tag contained in the first DNA templates to form second DNA templates containing a T7 promoter sequence (SEQ ID NO.: No. 3; AATTCTAATAC-GACTCACTATAGGGAGACGAAGACAGTAGACA for SEQ ID NO.: 2; SEQ ID NO.:19; AATTCTAATACGACT-CACTATAGGGAGAAGCCTGCACCAACAGTTAAC, SEQ ID NO.: 20: AATTCTAATACGACTCACTATAGG-GAGAAGCCTGCACCAACAGTTAACA and SEQ ID NO.: 21: AATTCTAATACGACTCACTATAGG-GAGAGCCTGCACCAACAGTTAAC-3'-C3 propyl spacer for SEQ ID NO.: 17; SEQ ID NO.:22: AATTCTAATAC-GACTCACTATAGGGAGAGCCTGCACCAA-CAGTTCACA for SEQ ID NO.:18).

For SEQ ID NO.: 17, three different second oligonucleotide templates were tested —SEQ ID NO.: 19 was considered the standard, SEQ ID NO.: 20 was longer by one nucleotide at its 3' end and SEQ ID NO.: 21 was blocked at its 3' terminus with a C3 propyl spacer.

Transcription of the resulting first DNA templates was then performed according to the teachings of Example 2 of the original patent application in order to synthesize amplified RNA. The RNA synthesized from each 50 ng cDNA tagging reactions was then subjected to a second round of transcription amplification following the teachings of Example 6 of the original patent application. The transcribed RNA after the second round for each reaction was purified (Qiagen Rneasy Kit) and the yields quantified at $A_{260}$ nm (Table 4). Except for the reaction containing the second oligonucleotide template with the blocked 3' terminus (SEQ ID NO.: 21), a similar quantity of transcribed RNA was obtained for each reaction showing comparable sensitivity for the different oligonucleotide sequence tags. The incomplete double-stranded second DNA templates formed using SEQ ID NO.: 21 resulted in 80%-90% less transcribed RNA, which was consistent with the findings of Example 2 above using Seq. ID. No. 2. Additionally, two different oligonucleotide synthesis of Seq. ID. No. 2 gave similar yields indicating that the oligonucleotides can be remade without any adverse effects.

Furthermore, a 200 ng aliquot of each transcribed RNA was analyzed by agarose gel electrophoresis and Northern blot hybridization to $^{32}P$ labeled cDNA probes specific for GAPDH. The electrophoretic profiles of the transcribed RNA for all the different conditions tested were similar and the hybridization pattern for GAPDH indicated largely the full-length product in each case (data not shown).

Thus, from this example it may be seen that the different oligonucleotide sequence tags did not adversely affect the tagging of the cDNA molecules and subsequent synthesis of transcribed RNA.

TABLE 4

Transcribed RNA Yields from the Different Oligonucleotide Sequence Tags

| Input Total RNA (ng) | Transcribed RNA Yields (μg) | | | | | |
|---|---|---|---|---|---|---|
| | Seq. ID. No. 2 | | Seq. ID. No. 17 | | | Seq. ID. No. 18 |
| | Synthesis 1 | Synthesis 2 | Seq. ID. No. 19 | Seq. ID. No. 20 | Seq. ID. No. 21 | Seq. ID. No. 22 |
| 50 | 71 | 78 | 78 | 56 | 8 | 55 |

I claim:

1. A method for adding a terminal sequence tag to a target DNA molecule, the method comprising:
   a) providing:
      1) a sample containing at least one target DNA molecule;
      2) a first oligonucleotide comprising:
         a) a 5' overhanging portion that exhibits a user-defined first sequence tag, wherein the 5' overhanging portion comprises deoxyribonucleotides;
         b) a 3' hybridizing portion that exhibits a sequence that is capable of hybridizing to the 3'-end of the target DNA molecule, wherein said 3' hybridizing portion comprises a ribonucleic acid section; and
         c) a blocked 3'-end; and
      3) a DNA polymerase;
   b) contacting the target DNA molecule with the first oligonucleotide under conditions allowing hybridization of the 3' hybridizing portion of the first oligonucleotide to the target DNA molecule;
   c) incubating the target DNA molecule to which the first oligonucleotide is hybridized with the DNA polymerase under conditions wherein the 3' end of the target DNA molecule is extended using the 5' overhanging portion of the first oligonucleotide as a template to generate a first DNA template that exhibits a terminal sequence tag that is complementary to the first sequence tag of the first oligonucleotide;
   d) removing the ribonucleic acid section of the first oligonucleotide that is hybridized to the target DNA molecule to generate a cleaved first oligonucleotide that has a 3' end that is capable of being extended by a DNA polymerase; and
   e) extending the 3'-end of the cleaved first oligonucleotide using the first DNA template as a template to generate a double-stranded DNA molecule comprising the first DNA template that exhibits the terminal sequence tag and a second DNA template that has the first sequence tag of the first oligonucleotide.

2. The method of claim 1, wherein the sample that contains at least one target DNA molecule provided in step a)1) contains a plurality of target DNA molecules and the first oligonucleotide provided in step a)2) comprises a plurality of first oligonucleotides, each of which comprises a 3' hybridizing portion that exhibits a sequence that is capable of hybridizing to the 3' end of at least one target DNA molecule.

3. The method of claim 1, wherein the 3' hybridizing portion of the first oligonucleotide comprises a random sequence.

4. The method of claim 1, wherein the at least one target DNA molecule is complementary DNA (cDNA) generated by reverse transcription of at least one RNA molecule.

5. The method of claim 4, wherein said at least one target DNA molecule comprises cDNA generated by reverse transcription of messenger RNA.

6. The method of claim 1, wherein at least one target DNA molecule is of unknown sequence.

7. The method of claim 1, wherein at least one target DNA molecule is of known sequence.

8. The method of claim 1, wherein the first sequence tag exhibited by the first oligonucleotide exhibits a sequence of one strand of an RNA polymerase promoter sequence.

9. The method of claim 8, wherein the method further comprises:
   amplifying RNA by contacting the double-stranded DNA comprising the second DNA template using an RNA polymerase that is capable of binding to the RNA polymerase promoter therein and incubating under in vitro transcription conditions wherein RNA is synthesized.

10. The method of claim 1, wherein the first sequence tag of the first oligonucleotide does not exhibit a sequence of an RNA polymerase promoter, wherein the method additionally provides a second oligonucleotide comprising, sequentially in a 5'->3' direction: (a) a 5'-overhanging portion that comprises a second sequence tag that exhibits a sequence of one strand of an RNA polymerase promoter; and (b) a 3' hybridizing portion that exhibits a sequence that is identical to a sequence exhibited by the first sequence tag of the 5' overhanging portion of the first oligonucleotide; and
   wherein the method further comprises the steps of:
   f) denaturing the first DNA template from the second DNA template obtained in step e);
   g) contacting the first DNA template with the second oligonucleotide under conditions allowing hybridization or annealing of the 3' hybridizing portion of the second oligonucleotide to the 3' end of the first DNA template that has the terminal sequence tag that is complementary to the first sequence tag of the first oligonucleotide;
   h) incubating the first DNA template to which the second oligonucleotide is hybridized with the DNA polymerase under conditions wherein the 3' end of the first DNA template is extended using the 5' overhanging portion of the second oligonucleotide as a template and the 3' end of the second oligonucleotide is extended using the first DNA template as a template to generate a new second DNA template, thereby generating double-stranded cDNA that contains a double-stranded RNA polymerase promoter;
   i) contacting the double-stranded cDNA with an RNA polymerase that is capable of binding to the RNA polymerase promoter therein and incubating under in vitro transcription conditions wherein RNA is synthesized.

11. The method of claim 1, wherein step d) of removing the ribonucleic acid section of the first oligonucleotide is performed with an enzyme.

12. The method of claim 11, wherein the enzyme is ribonuclease H.

* * * * *

SEQUENCE LISTING

<160> NUMBER OF SEQ ID NOS: 22

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
tvvvvvvvvv vvvvvvvvv v    21

<210> SEQ ID NO 2
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(23)
<223> OTHER INFORMATION: n is a, c, g, or t
<220> FEATURE:
<221> NAME/KEY: misc_feature
<222> LOCATION: (24)..(24)
<223> OTHER INFORMATION: The residue at this position is linked to a
      2'-O-Methyl and a 3'-C3 propyl spacer.

<400> SEQUENCE: 2
gacgaagaca gtagacannn nnnn                                                24

<210> SEQ ID NO 3
<211> LENGTH: 43
<212> TYPE: DNA
<213> ORGANISM: Artificial Sequence
<220> FEATURE:
<223> OTHER INFORMATION: Synthetic

<400> SEQUENCE: 3
aattctaata cgactcacta tagggagacg aagacagtag aca                           43

<210> SEQ ID NO 4
<211> LENGTH: 31
<212> TYPE: DNA
<213> ORGANISM: Artificial Sequence
<220> FEATURE:
<223> OTHER INFORMATION: Synthetic

<400> SEQUENCE: 4
ttggcgcgcc ttgggagacg aagacagtag a                                       31

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
catgtgggcc atgaggtcca ccac                                               24

<210> SEQ ID NO 6
<211> LENGTH: 32
<212> TYPE: DNA
<213> ORGANISM: Artificial Sequence
<220> FEATURE:
<223> OTHER INFORMATION: Synthetic

<400> SEQUENCE: 6
cgtcatactc ctgcttgctg atccacatct gc                                      32

<210> SEQ ID NO 7
<211> LENGTH: 36
<212> TYPE: DNA
<213> ORGANISM: Artificial Sequence
<220> FEATURE:
<223> OTHER INFORMATION: Synthetic

<400> SEQUENCE: 7
aaccctgcgg ccgccacatc tgctggaagg tggaca                                  36

<210> SEQ ID NO 8
<211> LENGTH: 18
<212> TYPE: DNA
<213> ORGANISM: Artificial Sequence
<220> FEATURE:
<223> OTHER INFORMATION: Synthetic

<400> SEQUENCE: 8
aatcactgga cgcgtggc                                                      18

<210> SEQ ID NO 9
<211> LENGTH: 19
<212> TYPE: DNA

```
<213> ORGANISM: Artificial Sequence
<220> FEATURE:
<223> OTHER INFORMATION: Synthetic

<400> SEQUENCE: 9
ggaaacagct atgaccatg                                                        19

<210> SEQ ID NO 10
<211> LENGTH: 80
<212> TYPE: DNA
<213> ORGANISM: Artificial Sequence
<220> FEATURE:
<223> OTHER INFORMATION: Synthetic

<400> SEQUENCE: 10
gggagacgaa gacagtagac actccgccgc cggcttacac tgcgcttctt gccgctcctc           60
cgtcgccgcc gcgtccttcg                                                       80

<210> SEQ ID NO 11
<211> LENGTH: 82
<212> TYPE: DNA
<213> ORGANISM: Artificial Sequence
<220> FEATURE:
<223> OTHER INFORMATION: Synthetic

<400> SEQUENCE: 11
gggagacgaa gacagtagac acactccgcc gccggcttac actgcgcttc ttgccgctcc           60
tccgtcgccg ccgcgtcctt cg                                                    82

<210> SEQ ID NO 12
<211> LENGTH: 80
<212> TYPE: DNA
<213> ORGANISM: Artificial Sequence
<220> FEATURE:
<223> OTHER INFORMATION: Synthetic

<400> SEQUENCE: 12
gggagacgaa gacagtagac acggggtcac acacacagtg cccatctatg agggctacgc           60
ccttccccac gccatcttgc                                                       80

<210> SEQ ID NO 13
<211> LENGTH: 80
<212> TYPE: DNA
<213> ORGANISM: Artificial Sequence
<220> FEATURE:
<223> OTHER INFORMATION: Synthetic

<400> SEQUENCE: 13
gggagacgaa gacagtagac attcaggcgg tgctgtcctt gtatgcatct gggcgcacca           60
ctggcattgt catggactct                                                       80

<210> SEQ ID NO 14
<211> LENGTH: 80
<212> TYPE: DNA
<213> ORGANISM: Artificial Sequence
<220> FEATURE:
<223> OTHER INFORMATION: Synthetic

<400> SEQUENCE: 14
gggagacgaa gacagtagac aagctaacag agagaagatg acgcagataa tgtttgaaac           60
cttcaatacc ccagccatgt                                                       80

<210> SEQ ID NO 15
```

```
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (44)..(49)
<223> OTHER INFORMATION: n = an equal mixture of ribonucleotides ATP,
      GTP, CTP and UTP
<220> FEATURE:
<221> NAME/KEY: misc_feature
<222> LOCATION: (50)..(50)
<223> OTHER INFORMATION: The residue at this position is linked to a
      2'-O-Methyl and a 3'-C3 propyl spacer.

<400> SEQUENCE: 15
aattctaata cgactcacta tagggagacg aagacagtag acannnnnnn              50

<210> SEQ ID NO 16
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (44)..(49)
<223> OTHER INFORMATION: n is a, c, g, or t
<220> FEATURE:
<221> NAME/KEY: misc_feature
<222> LOCATION: (50)..(50)
<223> OTHER INFORMATION: The residue at this position is linked to a
      2'-O-Methyl and a 3'-C3 propyl spacer.

<400> SEQUENCE: 16
aattctaata cgactcacta tagggagacg aagacagtag acannnnnnn              50

<210> SEQ ID NO 17
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(28)
<223> OTHER INFORMATION: n is a, c, g, or t
<220> FEATURE:
<221> NAME/KEY: misc_feature
<222> LOCATION: (29)..(29)
<223> OTHER INFORMATION: The residue at this position is linked to a
      2'-O-Methyl and a 3'-C3 propyl spacer.

<400> SEQUENCE: 17
gcctgcacca acagttaaca gannnnnnn                                     29

<210> SEQ ID NO 18
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(28)
<223> OTHER INFORMATION: n is a, c, g, or t
<220> FEATURE:
<221> NAME/KEY: misc_feature
<222> LOCATION: (29)..(29)
<223> OTHER INFORMATION: The residue at this position is linked to a
      2'-O-Methyl and a 3'-C3 propyl spacer.

<400> SEQUENCE: 18
```

```
gcctgcacca acagttcaca gannnnnnn                              29

<210> SEQ ID NO 19
<211> LENGTH: 47
<212> TYPE: DNA
<213> ORGANISM: Artificial Sequence
<220> FEATURE:
<223> OTHER INFORMATION: Synthetic

<400> SEQUENCE: 19
aattctaata cgactcacta tagggagagc ctgcaccaac agttaac          47

<210> SEQ ID NO 20
<211> LENGTH: 48
<212> TYPE: DNA
<213> ORGANISM: Artificial Sequence
<220> FEATURE:
<223> OTHER INFORMATION: Synthetic

<400> SEQUENCE: 20
aattctaata cgactcacta tagggagagc ctgcaccaac agttaaca         48

<210> SEQ ID NO 21
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (47)..(47)
<223> OTHER INFORMATION: The residue at this position is linked to a
      3'-C3 propyl spacer.

<400> SEQUENCE: 21
aattctaata cgactcacta tagggagagc ctgcaccaac agttaac          47

<210> SEQ ID NO 22
<211> LENGTH: 48
<212> TYPE: DNA
<213> ORGANISM: Artificial Sequence
<220> FEATURE:
<223> OTHER INFORMATION: Synthetic

<400> SEQUENCE: 22
aattctaata cgactcacta tagggagagc ctgcaccaac agttcaca         48
```